US012686657B2

(12) United States Patent
Kollias et al.

(10) Patent No.: US 12,686,657 B2
(45) Date of Patent: Jul. 21, 2026

(54) ANTI-INFLAMMATORY CARBOXAMIDE DERIVATIVES

(71) Applicant: BIOMEDCODE HELLAS SA, Vari (GR)

(72) Inventors: George Kollias, Vari (GR); Niki Karagianni, Vari (GR); Maria C. Denis, Vari (GR); Alexios N. Matralis, Vari (GR); Dimitra Papadopoulou, Vari (GR); Eleni Karkoulia, Vari (GR)

(73) Assignee: BIOMEDCODE HELLAS SA, Vari (GR)

( * ) Notice: Subject to any disclaimer, the term of this patent is extended or adjusted under 35 U.S.C. 154(b) by 381 days.

(21) Appl. No.: 18/549,986

(22) PCT Filed: Mar. 11, 2022

(86) PCT No.: PCT/EP2022/056349
§ 371 (c)(1),
(2) Date: Sep. 11, 2023

(87) PCT Pub. No.: WO2022/189636
PCT Pub. Date: Sep. 15, 2022

(65) Prior Publication Data

US 2024/0308954 A1 Sep. 19, 2024

(30) Foreign Application Priority Data

Mar. 12, 2021 (EP) .................................... 21162396

(51) Int. Cl.

| | |
|---|---|
| ***C07C 237/44*** | (2006.01) |
| ***A61K 31/166*** | (2006.01) |
| ***A61K 31/353*** | (2006.01) |
| ***A61K 31/44*** | (2006.01) |
| ***A61K 31/4418*** | (2006.01) |
| ***A61K 31/451*** | (2006.01) |
| ***A61K 31/495*** | (2006.01) |
| ***A61K 31/5375*** | (2006.01) |
| ***A61K 31/5377*** | (2006.01) |
| ***A61K 31/54*** | (2006.01) |
| ***A61P 29/00*** | (2006.01) |
| ***C07C 231/02*** | (2006.01) |
| ***C07D 211/38*** | (2006.01) |
| ***C07D 213/40*** | (2006.01) |
| ***C07D 213/82*** | (2006.01) |
| ***C07D 241/44*** | (2006.01) |
| ***C07D 295/135*** | (2006.01) |
| ***C07D 311/58*** | (2006.01) |
| ***C07D 471/04*** | (2006.01) |

(52) U.S. Cl.
CPC .......... *C07C 237/44* (2013.01); *A61K 31/166* (2013.01); *A61K 31/353* (2013.01); *A61K 31/44* (2013.01); *A61K 31/4418* (2013.01); *A61K 31/451* (2013.01); *A61K 31/495* (2013.01); *A61K 31/5375* (2013.01); *A61K 31/5377* (2013.01); *A61K 31/54* (2013.01); *A61P 29/00* (2018.01); *C07C 231/02* (2013.01); *C07D 211/38* (2013.01); *C07D 213/40* (2013.01); *C07D 213/82* (2013.01); *C07D 241/44* (2013.01); *C07D 295/135* (2013.01); *C07D 311/58* (2013.01); *C07D 471/04* (2013.01); *C07C 2601/02* (2017.05); *C07C 2601/04* (2017.05); *C07C 2601/08* (2017.05); *C07C 2601/14* (2017.05); *C07C 2601/18* (2017.05)

(58) Field of Classification Search
CPC .................................................... C07C 237/44
See application file for complete search history.

(56) References Cited

U.S. PATENT DOCUMENTS

2013/0096319 A1 4/2013 Paghdar et al.

FOREIGN PATENT DOCUMENTS

| | | | |
|---|---|---|---|
| WO | 95/18104 | A1 | 7/1995 |
| WO | 2006/112828 | A1 | 10/2006 |
| WO | 2009/138378 | A1 | 11/2009 |
| WO | 2014/097140 | A1 | 6/2014 |

OTHER PUBLICATIONS

Albericio, Fernando et al., "Choosing the Right Coupling Reagent for Peptides. A Twenty-Five-Year Journey", Org. Process Res. Dev., 2018, 22, 7, pp. 760-772, (https://doi.org/10.1021/acs.oprd.8b00159).
Armaka, Maria et al., "A standardized protocol for the isolation and culture of normal and arthritogenic murine synovial fibroblasts", Protocol Exchange, 2-5 (2009); (https://doi.org/10.1038/nprot.2009.102).
Becker, Daniel P. et al., "Pyrrolizidine esters and amides as 5-HT4 receptor agonists and antagonists", Journal of Medicinal Chemistry, 2006, vol. 49, No. 3, pp. 1125-1139.
Estrada, Anthony A. et al., "Discovery of Highly Potent, Selective, and Brain-Penetrable Leucine-Rich Repeat Kinase 2 (LRRK2) Small Molecule Inhibitors", Journal of Medicinal Chemistry, 2012, vol. 55, No. 22, pp. 9416-9433.
Feoktistova, Maria et al., "Crystal Violet Assay for Determining Viability of Cultured Cells", Cold Spring Harb Protoc, 2016(4), pp. 343-346 (doi:10.1101/pdb.prot087379).
Jiménez-García, Lidia et al., "Thioglycollate-elicited Peritoneal Macrophages Preparation and Arginase Activity Measurement in IL-4 Stimulated Macrophages", Bio-protocol 5(17), 2015, pp. 1-4 (DOI:10.21769/BioProtoc.1585).

(Continued)

*Primary Examiner* — Yong S. Chong
(74) *Attorney, Agent, or Firm* — Chrisman Gallo Tochtrop LLC

(57) ABSTRACT

A compound of formula (I) or a pharmaceutically acceptable salt, hydrate, or isomer thereof. Pharmaceutical compositions comprising the compounds of formula (I) as well as their use in therapy, particularly in the treatment of inflammatory conditions. Advantageously, the compounds show a broad and robust anti-inflammatory effect, and are therapeutically safe.

14 Claims, No Drawings

(56) References Cited

OTHER PUBLICATIONS

Keffer, Jeanne et al., "Transgenic mice expressing human tumour necrosis factor: a predictive genetic model of arthritis", The EMBO Journal, vol. 10, No. 13, pp. 4025-4031, 1991.
Matikonda, Siddharth S. et al., "Mechanistic Evaluation of Bioorthogonal Decaging with trans-Cyclooctene: the Effect of Fluorine Substituents on Aryl Azide Reactivity and Decaging from the 1,2,3-Triazoline", Bioconjugate Chem., 2018, 29, pp. 324-334, (DOI: 10.1021/acs.bioconjchem.7b00665).
Rassias, Geracimos et al., "Investigation of Synthetic Routes to a Key Benzopyran Intermediate of a 5HT4 Agonist", Organic Process Research & Development, 2010, vol. 14, No. 1, pp. 92-98.
Seemann, Semjon et al., "Comprehensive comparison of three different animal models for systemic inflammation", Journal of Biomedical Science, 2017, 24(1):60, pp. 1-17 (doi.org/10.1186/s12929-017-0370-8).
Stortz, Julie A. et al., "Murine Models of Sepsis and Trauma: Can We Bridge the Gap?", ILAR Journal, 2017, vol. 58, No. 1, pp. 90-105 (doi: 10.1093/ilar/ilx007).
Vasilopoulos, V. et al., "Actin cytoskeleton dynamics linked to synovial fibroblast activation as a novel pathogenic principle in TNF-driven arthritis", Ann Rheum Dis, 2007;66(Suppl III):iii23-iii28 (doi: 10.1136/ard.2007.079822).
International Search Report of International Application PCT/EP2022/056349, Dated Jun. 22, 2022, 12 pages.

ANTI-INFLAMMATORY CARBOXAMIDE DERIVATIVES

CROSS-REFERENCE TO RELATED APPLICATIONS

This is a National Stage application of PCT international application PCT/EP2022/056349, filed on Mar. 11, 2022, which claims the benefit of European Patent Application EP21162396.2, filed Mar. 12, 2021, both of which are incorporated herein by reference in their entirety.

TECHNICAL FIELD

The present invention relates to the field of medicine and therapy, particularly of the treatment of inflammatory conditions. In particular, the present invention provides compounds of formula (I), processes for their preparation, pharmaceutical compositions comprising these compounds and their use in the treatment of an inflammatory condition, particularly an arthritic condition.

BACKGROUND ART

Inflammation is a localized protective response, elicited by injury or destruction of tissues, which serves to destroy, dilute or wall off both the injurious agent and the injured tissue. It is characterized by fenestration of the microvasculature, leakage of the elements of blood into the interstitial spaces, and migration of leukocytes into the inflamed tissue. On a macroscopic level, this is usually accompanied by the familiar clinical signs of erythema, edema, hyperalgesia (tenderness), and pain.

During this complex response, chemical mediators such as histamine, 5-hydroxytryptamine, various chemotactic compositions, bradykinin, leukotrienes, and prostaglandins are liberated locally. Phagocytic cells migrate into the area, and cellular lysosomal membranes may be ruptured, releasing lytic enzymes. All of these events can contribute to the inflammatory response. Inflammation resulting from rheumatoid arthritis likely involves the combination of an antigen with an antibody complement causing the local release of chemotactic and chemoactivating compositions that attract leukocytes. The leukocytes phagocytose the complexes of antigen-antibody and complement, and also release the many enzymes contained in their lysosomes. These lysosomal enzymes then cause injury to cartilage and other tissues, and this furthers the degree of inflammation. Cell-mediated immune reactions may also be involved. Prostaglandins, which are key intracellular regulators of cellular function, are also released during this process.

The inflammatory response is any response characterized by inflammation as defined above. It is well known that the inflammatory response causes much of the physical discomfort (i.e., pain and loss of function) that has come to be associated with different diseases and injuries. In order to treat inflammatory related disorders, it is a common medical practice to administer pharmacological agents that reduce the physical discomfort of the inflammatory response. Agents having these properties are classified as anti-inflammatory. Anti-inflammatory drugs are used for the treatment of a wide spectrum of disorders, and the same drugs are often used to treat different diseases. Treatment with anti-inflammatory drugs is not for the disease, but most often for the symptom (i.e., inflammation).

The anti-inflammatory, analgesic, and anti-pyretic drugs are a heterogeneous group of compounds, often chemically unrelated, which nevertheless share certain therapeutic actions and side-effects. Corticosteroids represent the most widely-used class of compounds for the treatment of inflammation. Proteolytic enzymes represent another class of compounds that are thought to have anti-inflammatory effects. Hormones that directly or indirectly cause the adrenal cortex to produce and secrete steroids represent another class of anti-inflammatory compounds. Unfortunately, the natural and synthetic corticosteroid preparations cause a number of severe side effects, including elevation of blood pressure, salt and water retention, kidney damage and increased potassium and calcium excretion. Moreover, corticosteroids may mask the signs of infection and enhance dissemination of infectious microorganisms. These hormones are considered unsafe for use in pregnant women, and long-term corticosteroid treatment has been associated with gastric hyperactivity and/or peptic ulcers. Treatment with corticosteroids may also aggravate diabetes mellitus, requiring higher doses of insulin, and may produce psychotic disorders. Hormonal anti-inflammatory agents which indirectly increase the production of endogenous corticosteroids have the same potential for adverse side-effects.

Another class of drugs are the disease modifying anti-rheumatic drugs (DMARDS). An example of these is methotrexate, an anti-metabolite drug, which is widely used for the treatment of rheumatoid arthritis, psoriatic arthritis and psoriasis. Methotrexate has been successful in the treatment of these diseases, but can cause substantial side effects, such as severe skin reaction, infections such as pneumonia, severe damage to liver, kidneys, lungs and gastrointestinal tract.

A number of DMARD pharmaceutical agents containing gold are also used in the treatment of inflammatory conditions, particularly rheumatoid arthritis. Examples of such agents include gold sodium thiomalate and auranofin. Potential side effects from being treated with anti-inflammatory gold agents are oral ulcers, altered taste, serious skin rashes, renal problems, inflammation of the intestines (enterocolitis), liver injury and lung disease. Furthermore, resistance to gold has been known to develop in patients.

A further class of drugs are the non-steroidal anti-inflammatory drugs (NSAED's). These are used to alleviate symptoms and includes the Cox 2 inhibitors "VIOXX"®, (a registered trademark of Merck & Co., Inc.) and "CELEBREX"®, (a registered trademark of G.D. Searle & Co).

In spite of the efforts made, however, the current therapies have several drawbacks: lack of efficacy, development of resistance, unacceptable side-effects and expense of existing treatments.

Therefore, there is still the need of further anti-inflammatory agents.

SUMMARY OF INVENTION

The present inventors have found compounds with a broad anti-inflammatory spectrum.

In particular, the present inventors have found that the compounds of the invention, when administered, elicit a multi-target action, significantly affecting several of the cytokines and chemokines involved in the inflammation process.

In this regard, the inventors tested the anti-inflammatory potential of the compounds of the invention on inflammatory cytokines and chemokines secreted from activated macrophages, concluding that the tested compounds could effectively ameliorate their production (see Tables 6a and 6b below).

These findings were also confirmed testing the compounds on activated synovial fibroblasts (SFs), which are well-known as playing an instrumental role in inflammatory conditions such as arthritis, particularly rheumatoid arthritis. As it is shown in Table 7 below, it was found that the compounds of the invention, at very low concentration, were able to remarkably downregulate the level of two pro-inflammatory chemokines, CCL5 and CCL20.

The polyvalency of the compounds of the invention in modulating the inflammatory response was also tested using a commercially pro-inflammatory chemokine panel (Legendplex). It was found that the tested compounds were able to remarkably ameliorate the levels of the secreted chemokines EOTAXIN, KC, LIX MCP1 and MIP1β of activated SFs (Table 8). The fact that the compounds of the invention can provide such response, in a so remarkable way, over several chemokines involved in the inflammatory process is indicative of the strong therapeutic response which can be achieved with the administration of the compounds of the invention.

This strong effect would explain the remarkable reduction in CCL5 and CCL20, administering low concentrations of the compounds. For example, a reduction in chemokine levels close up to a 30% or less can be achieved administering a concentration of 10 uM. Remarkably, it has also been found that the effective doses are far from the cytotoxic concentrations, making the compounds of the invention safe for their use in therapy.

Therefore, the compounds of the invention not only provide a broad and robust anti-inflammatory effect, affecting several chemokines and cytokines, but also they are therapeutically safe.

The above were confirmed in the in vivo tests performed by the present inventors using an acute systemic inflammation model. As it is shown in Tables 11 and 12 below, the compounds of the invention could effectively reduce the levels of several inflammatory cytokines, namely IL1α, IL6, IL17A, IL1β, IL-23, TNF-α, IFN-γ, IL12p70, IL-1β, IL-27, IL-17A, GM-CSF, and KC while they increased the levels of the cytokine IL10 which is known to have potent anti-inflammatory activities.

Not only that, but also, the compounds of the invention were also able to reduce the levels of chemokines MCP-1, MIP-1A, MIP-1B, IP-10, and MDC.

Overall, the above data show the versatility of the compounds of the invention, at low concentrations, in modulating the levels of different cytokines and chemokines using different in vitro and in vivo inflammatory models, being potential candidates as anti-inflammatory drugs.

Thus, in a first aspect the present invention provides a compound of formula (I):

(I)

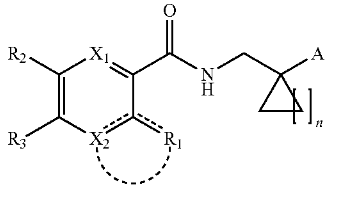

or a pharmaceutically acceptable salt, hydrate, or isomer thereof, wherein:

$R_1$ represents halogen; $-OR_4$; $(C_1-C_{10})$alkyl; or $(C_1-C_{10})$alkyl substituted with one or more substituents, the same or different, selected from OH, halogen, $(C_1-C_6)$alkyl, $-O-(C_1-C_6)$alkyl, nitro, cyano, and halogen; or, alternatively, $R_1$ together with $X_2$ forms an aromatic, saturated or partially saturated known ring, the ring having 5 or 6 members selected from the group consisting of: $-C(R_x)_2-$, $-CR_x-$, $-N-$, $-NR_x-$, S, and O;

--- represents a single bond or a double bond:

$R_2$ represents $-OH$; halogen; $(C_1-C_{10})$alkyl; $(C_1-C_{10})$alkyl substituted with one or more substituents, the same or different, selected from OH, halogen, $(C_1-C_6)$alkyl, $-O-(C_1-C_6)$alkyl, nitro, cyano, and halogen; $-S(O)_2R_4$; an aromatic known ring system comprising 5 or 6 members selected from $-CR_a-$, and $-N-$;

$R_3$ represents $-NR_5R_6$, being $R_5$ and $R_6$ the same or different and being selected from $-H$, $(C_1-C_{10})$alkyl, $(C_3-C_{10})$cycloalkyl, and an aromatic known ring system comprising 5 or 6 members selected from $-CR_b-$, and $-N-$; or, alternatively, $R_2$ together with $R_3$ form an aromatic, saturated or partially saturated known ring, the ring having 5 or 6 members selected from $-C(R_y)_2-$, $-CR_y-$, $-N-$, $-NR_y$, $-S-$, and $-O-$;

A is a known ring system having from 1 to 3 rings and comprising from 4 to 14 members, each one of the members being selected from, $-C(R_z)_2-$, $-CR_z-$, $-N-$, $-NR_z-$, $-S-$, $-Se-$, $-SO_2$, $-SeO_2$, and $-O-$; the rings being saturated, partially unsaturated, or aromatic; and being fused or isolated; or, alternatively, A represents $-NR_c$-A', wherein $R_c$ represents $-H$ or $(C_1-C_{10})$alkyl, particularly $-H$; and A' is a known ring system having from 1 to 3 rings and comprising from 4 to 14 members, each one of the members being selected from, $-C(R_z)_2-$, $-CR_z-$, $-N-$, $-NR_z-$, $-S-$, $-Se-$, $-SO_2$, $-SeO_2$, and $-O-$; the rings being saturated, partially unsaturated, or aromatic; and being fused or isolated;

n represents a enter value comprised from 1 to 7;

$X_1$ and $X_2$ are the same or different and represent C or N atom;

$R_4$ represents $-H$; $(C_1-C_{10})$ alkyl; or $(C_1-C_{10})$ alkyl substituted with one or more substituents, the same or different, selected from OH, halogen, $(C_1-C_6)$alkyl, $-O-(C_1-C_6)$alkyl, nitro, cyano, and halogen;

the term "$(C_3-C_{10})$cycloalkyl" refers to a saturated carbocyclic ring containing from 3 to 10 carbon atoms;

each one of $R_a$ is independently selected from the group consisting of $-H$, $-OH$, halogen, $(C_1-C_6)$alkyl, and $(C_1-C_6)$alkyl substituted with one or more substituents, the same or different, selected from: OH, halogen, $(C_1-C_6)$alkyl, $-O-(C_1-C_6)$alkyl, nitro, cyano, and halogen;

each one of $R_b$ is independently selected from the group consisting of $-H$, $-OH$, halogen, $(C_1-C_6)$alkyl, and $(C_1-C_6)$alkyl substituted with one or more substituents, the same or different, selected from: OH, halogen, $(C_1-C_6)$alkyl, $-O-(C_1-C_6)$alkyl, nitro, cyano, and halogen;

$R_t$ represents $(C_1-C_{10})$ alkyl;

each one of the $R_x$ is independently selected from the group consisting of $-H$, $-OH$, $(C_1-C_6)$alkyl, $(C_1-C_6)$haloalkyl, $-O-(C_1-C_6)$alkyl, nitro, $-NR_7-$, $-NR_8R_9$, and halogen;

each one of the Ry is independently selected from the group consisting of —H, —OH, $(C_1\text{-}C_6)$alkyl, $(C_1\text{-}C_6)$ haloalkyl, —O—$(C_1\text{-}C_6)$alkyl, nitro, —$NR_{10}$—, —$NR_{11}R_{12}$, and halogen;

each one of the Rz is independently selected from the group consisting of —H, —OH, $(C_1\text{-}C_6)$alkyl, $(C_1\text{-}C_6)$ haloalkyl, —O—$(C_1\text{-}C_6)$alkyl, —O—$(C_1\text{-}C_6)$haloalkyl, nitro, —$NR_{13}$—, —$NR_{12}R_{15}$, and halogen;

$R'_z$ is selected from the group consisting of $(C_1\text{-}C_6)$alkyl and $(C_1\text{-}C_6)$haloalkyl; and each one of $R_7$ to $R_{15}$ is independently selected from the group consisting of H, $(C_1\text{-}C_6)$alkyl, $(C_1\text{-}C_6)$haloalkyl, and —O—$(C_1\text{-}C_6)$alkyl.

In a second aspect the present invention provides a process for the preparation of a compound of formula (I) as defined in the first aspect of the invention, the process comprising an amide coupling reaction between the carboxylic acid group of a compound of formula (II) and the amine group of a compound of formula (III):

(II)

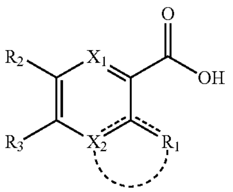

(III)

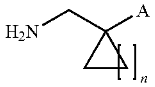

wherein $R_1$ to $R_3$, A, $X_1$, $X_2$ and n are as defined in the first aspect of the invention, in the presence of a polar solvent comprising one or more coupling agents.

In a third aspect the present invention provides a pharmaceutical composition comprising a therapeutically effective amount of a compound of formula (I) as defined in the first aspect of the invention, together with one or more pharmaceutically acceptable excipients or carriers.

In a fourth aspect the present invention provides a compound of formula (I) as defined in the first aspect of the invention for use in therapy.

As it has been stated above, the compounds have been tested in vitro, using cell types known to play a leading role in systemic inflammation (i.e. macrophages) but also in inflammatory conditions such as arthritis (i.e. synovial fibroblasts, SFs), but also in vivo, using a lipopolysaccharide (LPS) model of acute systemic inflammation. Administration of the endotoxin Lipopolysaccharide (LPS) to mice induces acute inflammatory responses similar to the inflammatory response that occurs during the early stages of septic shock. Shortly after administration of the endotoxin, cytokines and chemokines including TNF-a and IL-6 are released. This model is fast, cost-effective and widely used for screening of anti-inflammatory properties of test items aimed for treatment of a number of inflammatory conditions, including autoimmune conditions.

As it has been concluded below, the compounds of the invention are able to provide a broad anti-inflammatory effect both in the arthritic and systemic models.

Thus, in a fifth aspect the present invention provides a compound of formula (I) as defined in the first aspect of the invention, for use in the treatment of an inflammatory condition. This aspect can alternatively be formulated as the use of a compound of formula (I) as defined in the first aspect of the invention for the manufacture of a medicament for the treatment of an inflammatory condition. This aspect can alternatively be formulated as a method for the treatment of an inflammatory condition, the method comprising administering a therapeutically effective amount of a compound as defined in the first aspect of the invention to a subject in need thereof or of the pharmaceutical composition as defined in the third aspect of the invention.

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

For the purposes of the present invention, any ranges given include both the lower and the upper end-points of the range.

In a first aspect the present invention provides a compound of formula (I), a pharmaceutically acceptable salt, hydrate or isomer thereof.

In the present invention, the term "pharmaceutically acceptable salt" refers to a salt of a compound of the invention which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Examples of appropriate inorganic acids include hydrochloric acid, hydrobromic acid, hydroiodic acid, nitric acid, perchloric acid, sulfuric acid or phosphoric acid. Examples of appropriate organic acids include methansulfonic acid, trifluoromethansulfonic acid, ethansulfonic acid, benzenesulfonic acid, p-toluenesulfonic acid, fumaric acid, citric acid, oxalic acid, acetic acid and maleic acid, among others.

In the present invention, the term "hydrate" means a solvate wherein the solvent molecule(s) is/are $H_2O$.

In the present invention, the term "isomer" encompasses stereoisomers, optical isomers; enantiomers, diastereoisomes and racemic mixtures, esters, tautomers, individual isomers, and mixtures of isomers thereof.

The term "isomers" means compounds having the same number and kind of atoms, and hence the same molecular weight, but differing with respect to the arrangement or configuration of the atoms in space.

The terms "stereoisomer" or "optical isomer" mean a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure exist in the compounds of the invention which may give rise to stereoisomerism, the invention contemplates stereoisomers and mixtures thereof. The compounds of the invention and their salts include asymmetric carbon atoms and may therefore exist as single stereoisomers, racemates, and as mixtures of enantiomers and diastereomers. If desired, however, such compounds can be prepared or isolated as pure stereoisomers, i.e., as individual enantiomers or diastereomers, or as stereoisomer-enriched mixtures. Individual stereoisomers of compounds can be prepared by synthesis from optically active starting materials containing the desired chiral centers or by preparation of mixtures of enantiomeric products followed by separation or resolution, such as conversion to a mixture of diastereomers followed by separation or recrystallization, chromatographic techniques, use of chiral resolving agents, or direct separation of the enantiomers on chiral chromatographic columns. Starting compounds of particular stereochemistry are either commercially available or are made by the methods described below and resolved by techniques well-known in the art.

The term "enantiomers" means a pair of stereoisomers that are non-superimposable mirror images of each other.

The terms "diastereoisomers" or "diastereomers" mean optical isomers which are not mirror images of each other.

The terms "racemic mixture" or "racemate" mean a mixture containing equal parts of individual enantiomers.

Some of the compounds of the invention can exist in more than one tautomeric form. As mentioned above, the compounds of the invention include all such tautomers.

In the context of the invention, the terms "halo" and "halogen" are used interchangeably and refer to a halogen group selected from chloro, fluoro, bromo and iodo.

In the context of the invention, the term "alkyl" refers to a saturated linear or branched hydrocarbon chain containing the number of carbon atoms indicated in the claims and in the description. Examples of alkyl groups include, but are not limited to: methyl, ethyl, propyl, iso-propyl, butyl, isobutyl, tert-butyl, pentyl, hexyl, heptyl, octyl, nonanyl and decanyl.

In the context of the invention, the term "$(C_1\text{-}C_6)$haloalkyl" refers to a saturated linear or branched hydrocarbon chain containing from 1 to 6 carbon atom members, wherein at least one of the carbon atoms is substituted by at least one halogen.

Examples of alkyloxy groups ("—O—$(C_1\text{-}C_6)$alkyl") include, but are not limited to, methoxy, ethoxy, n-propoxy, isopropoxy, n-butoxy, isobutoxy, sec-butoxy and tert-butoxy.

The term "known ring system" refers to a ring system which is known in the art and so intends to exclude those ring systems that are not chemically possible.

According to the present invention a ring system formed by "isolated" rings means that the ring system is formed by two, three or four rings and said rings are bound via a bond from the atom of one ring to the atom of the other ring. The term "isolated" also embraces the embodiment in which the ring system has only one ring. Illustrative non-limitative examples of known ring systems consisting of one ring are those derived from: cyclopropyl, cyclobutyl, cyclopentyl, cyclohexyl, cycloheptyl, cyclopropenyl, cyclobutenyl, cyclopentenyl, phenyl, biphenylyl, and cycloheptenyl.

According to the present invention the expression "fused rings" encompasses rings totally fused, partially fused or spiro fused.

According to the present invention, when the ring system is "totally fused" it means that the ring system is formed by two, three or four rings in which two or more atoms are common to two adjoining rings. Illustrative non-limitative examples are 1,2,3,4-tetrahydronaphthyl, 1-naphthyl, 2-naphthyl, anthryl, or phenanthryl.

According to the present invention when the ring system is "partially fused", it means that the ring system is formed by three or four rings, being at least two of said rings totally fused (i.e. two or more atoms being common to the two adjoining rings) and the remaining ring(s) being bound via a bond from the atom of one ring to the atom of one of the fused rings.

According to the present invention when the ring system is "spiro fused", it means that the ring system comprises at least two rings sharing a common atom. The simplest spiro compounds are bicyclic (having just two rings), or have a bicyclic portion as part of the larger ring system, in either case with the two rings connected through the defining single common atom. Spiro compounds may be fully carbocyclic (all carbon) or heterocyclic (having one or more non-carbon atom forming part of the backbone of the rings).

In one embodiment of the first aspect of the invention, optionally in combination with any of the embodiments provided above or below, the compound is one of formula (Ia):

(Ia)

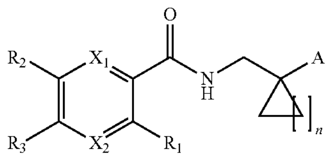

wherein $R_1$, $R_2$, $R_3$, $X_1$, $X_2$, A and n are as defined above.

In another embodiment of the first aspect of the invention, optionally in combination with any of the embodiments provided above or below, $R_1$ is selected from —OH, —O—$(C_1\text{-}C_{10})$alkyl, and halogen.

In another embodiment of the first aspect of the invention, optionally in combination with any of the embodiments provided above or below, $R_1$ together with $X_2$ forms a partially saturated or aromatic ring having 5 or 6 members, the members being as defined above. In one embodiment, optionally in combination with any of the embodiments provided above or below, $R_1$ together with $X_2$ forms a partially saturated ring having 5 or 6 members, wherein one or two of the members are the same or different and are selected from —N—, —$NR_x$—, —S— and —O—, and the remaining members are selected from —CH— and —$CH_2$—.

In one embodiment, optionally in combination with any of the embodiments provided above or below, $R_1$ together with $X_2$ forms a partially saturated ring having 5 or 6 members, the members being as defined above. In another embodiment, optionally in combination with any of the embodiments provided above or below, $X_2$ represents C and, together with $R_1$, forms a partially saturated known ring having 5 or 6 members selected from CH, $CH_2$, N, NH, O and S. In another embodiment, optionally in combination with any of the embodiments provided above or below, $X_2$ represents C and, together with $R_1$, forms a partially saturated ring having 5 or 6 members, wherein at least one of the members is N, NH or O, and the remaining members are selected from —CH— and —$CH_2$—. In another embodiment, optionally in combination with any of the embodiments provided above or below, $X_2$ represents C and, together with $R_1$, forms a partially saturated ring having 5 or 6 members, particularly 6 members, one of the members being O and the other members being selected from —CH— and —$CH_2$—.

Alternatively, in another embodiment, optionally in combination with any of the embodiments provided above or below, $R_1$ together with $X_2$ forms an aromatic ring having 5 or 6 members, the members being as defined above. In another embodiment, optionally in combination with any of the embodiments provided above or below, $R_1$ together with $X_2$ forms an aromatic ring having 5 or 6 members, wherein at least one of the members is N. In another embodiment, optionally in combination with any of the embodiments provided above or below, $X_2$ represents N and, together with $R_1$, forms an aromatic ring having 5 or 6 members, as defined above. In another embodiment, optionally in combination with any of the embodiments provided above or below, $X_2$ represents N and, together with $R_1$, forms an aromatic ring having 5 or 6 members, as defined above, wherein two of the members are N and the remaining members are as defined above. In another embodiment, optionally in combination with any of the embodiments provided above or below, $X_2$ represents N and, together with $R_1$, forms an aromatic ring having 5 or 6 members, as defined above, wherein two of the members are N and the remaining members are CH, such as an imidazo ring.

In another embodiment, optionally in combination with any of the embodiments provided above or below, $R_2$ is an aryl and represents an aromatic ring system consisting of one ring having 5 or 6 members selected from CH, and N, which is optionally substituted with one more halogen atoms.

Alternatively, in another embodiment, optionally in combination with any of the embodiments provided above or below, $R_2$ represents halogen or $—S(O)_2R_t$. $R_t$ being as defined above.

In another embodiment, optionally in combination with any of the embodiments provided above or below, $R_3$ represents $—NR_6R_7$, being $R_6$ and $R_7$ the same. In another embodiment, optionally in combination with any of the embodiments provided above or below, $R_6$ and $R_7$ are independently selected from H and $(C_1\text{-}C_{10})$alkyl. In another embodiment, optionally in combination with any of the embodiments provided above or below, $R_3$ represents $—NR_6R_7$, $R_6$ and $R_7$ representing H.

Alternatively, in another embodiment, optionally in combination with any of the embodiments provided above or below, $R_3$ together with $R_2$ forms an aromatic or partially saturated known ring, the ring having 5 or 6 members as defined above. In one embodiment, optionally in combination with any of the embodiments provided above or below, $R_2$ together with $R_3$ forms an aromatic or partially saturated known ring, the ring having 5 or 6 members as selected from CH, C, NH, N, S, and O. In another embodiment, optionally in combination with any of the embodiments provided above or below, $R_2$ together with $R_3$ form an aromatic ring having 5 or 6 members as defined above. In another embodiment, optionally in combination with any of the embodiments provided above or below, $R_2$ together with $R_3$ form an aromatic ring having 5 or 6 members selected from $—C(R_y)—$, particularly —CH—, and N. In another embodiment, optionally in combination with any of the embodiments provided above or below, $R_2$ together with $R_3$ form an aromatic ring having 5 or 6 $—C(R_y)—$ members, particularly the aromatic ring consists of 6 $C(R_y)—$ members, particularly the aromatic ring is a phenyl.

In another embodiment, optionally in combination with any of the embodiments provided above or below, $R_1$ is $—O—(C_1\text{-}C_{10})$alkyl and $R_2$ is halogen.

In another embodiment, optionally in combination with any of the embodiments provided above or below, $R_1$ is $—O—(C_1\text{-}C_{10})$alkyl, $R_2$ is halogen or $—SO_2R_t$, and $R_3$ is $—NH_2$.

In another embodiment, optionally in combination with any of the embodiments provided above or below, $R_1$ is $—O—(C_1\text{-}C_{10})$alkyl, $R_2$ is halogen, $R_3$ is $—NH_2$ and n is 6.

In another embodiment, optionally in combination with any of the embodiments provided above or below, A is selected from:

i) a known aryl ring comprising 5 or 6 members, particularly 6 members, as defined in claim 1, particularly from $—CR_z—$, —N—, —S—, and —O—, wherein each one of the $R_z$ is independently selected from: H, —OH, $(C_1\text{-}C_6)$haloalkyl, and halogen; and ii) a saturated ring comprising from 4 to 8 members, particularly 6 members, as defined above; particularly from $—C(R_z)_2—$, $—NR'_z—$, —S—, —Se—, $—SO_2$, and —O—, wherein each one of the $R_z$ is independently selected from: H, $(C_1\text{-}C_6)$alkyl, and halogen; R'z represents $(C_1\text{-}C_6)$alkyl.

In one embodiment, optionally in combination with any of the embodiments provided above or below, A is a known ring system consisting of one ring having 6 members as defined above.

In one embodiment, optionally in combination with any of the embodiments provided above or below, A is a saturated known ring comprising 5 or 6 members, particularly 6 members, each one of the members being independently selected from $—C(R_z)_2—$, $—NR'_z—$, —S—, and —O—, each one of the Rz is independently selected from: H, $(C_1\text{-}C_6)$alkyl, and halogen; and $R'_z$ represents $(C_1\text{-}C_6)$alkyl In another embodiment, optionally in combination with any of the embodiments provided above or below, A is a saturated known ring having 6 members, each one of the members being independently selected from $—C(R_z)_2—$, $—NR'_z—$, —S—, and —O—, each one of the $R_z$ is independently selected from: H, $(C_1\text{-}C_6)$alkyl, and halogen; and $R'_z$ represents $(C_1\text{-}C_6)$alkyl.

In another embodiment, optionally in combination with any of the embodiments provided above or below, A is a known 6-membered ring selected from:

a known aryl wherein one of the members is —N—, and the other members forming the 6-membered ring are $—CR_z—$, each one of the $R_z$ being independently selected from: H, $(C_1\text{-}C_6)$haloalkyl, and halogen;

a known aryl ring having 6 $—CR_z—$ members, each one of the $R_z$ being independently selected from: H, $(C_1\text{-}C_6)$haloalkyl, $—NR_7—$, and halogen; and a saturated known ring, wherein one or two of the members are selected from $—NR'_z—$, —S—, and —O— and the other members forming part of the ring represent $—C(R_z)_2—$, each one of the $R_z$ being independently selected from: H, $(C_1\text{-}C_6)$alkyl, and halogen; and $R'_z$ represents $(C_1\text{-}C_6)$alkyl.

In another embodiment, optionally in combination with any of the embodiments provided above or below, $R_1$ is $—O—(C_1\text{-}C_{10})$alkyl, $R_2$ is halogen or $—SO_2R_t$, and A represents a saturated known ring comprising 5 or 6 members, particularly 6 members, each one of the members being independently selected from $—C(R_z)_2—$, $—NR'_z—$, —S—, and —O—, particularly from $—C(R_z)_2—$, $—NR'_z—$, and —O—, each one of the $R_z$ being independently selected from: H, $(C_1\text{-}C_6)$alkyl, and halogen; particularly all $R_z$ are H; and $R'_z$ represents $(C_1\text{-}C_6)$alkyl.

In another embodiment, optionally in combination with any of the embodiments provided above or below, $R_1$ is $—O—(C_1\text{-}C_{10})$alkyl, $R_2$ is halogen or $—SO_2R_t$, $R_3$ is $NH_2$, and A represents a saturated known ring comprising 5 or 6 members, particularly 6 members, each one of the members being independently selected from $—C(R_z)_2—$, $—NR'_z—$, —S—, and —O—, particularly from —$C(R_z)_2$—, —$NR'_z$—, and —O—, each one of the $R_z$ being independently selected from: H, $(C_1-C_6)$alkyl, and halogen; particularly all $R_z$ are H; and $R'_z$ represents $(C_1-C_6)$alkyl.

In another embodiment, optionally in combination with any of the embodiments provided above or below, $R_1$ is —O—$(C_1-C_{10})$alkyl, $R_2$ is halogen or —$SO_2R_t$, n is 6, and A represents a saturated known ring comprising 5 or 6 members, particularly 6 members, each one of the members being independently selected from —$C(R_z)_2$—, —$NR'_z$—, —S—, and —O—, particularly from —$C(R_z)_2$—, —$NR'_z$—, and —O—, each one of the $R_z$ being independently selected from: H, $(C_1-C_6)$alkyl, and halogen; particularly all $R_z$ are H; and $R'_z$ represents $(C_1-C_6)$alkyl.

In another embodiment, optionally in combination with any of the embodiments provided above or below, $R_1$ is —O—$(C_1-C_{10})$alkyl, $R_2$ is halogen or —$SO_2R_t$, $R_3$ is $NH_2$, n is 6, and A represents a saturated known ring comprising 5 or 6 members, particularly 6 members, each one of the members being independently selected from —$C(R_z)_2$—, —$NR'_z$—, —S—, and —O—, particularly from —$C(R_z)_2$—, —$NR'_z$, and —O—, each one of the $R_z$ being independently selected from: H, $(C_1-C_6)$alkyl, and halogen; particularly all $R_z$ are H; and $R'_z$ represents $(C_1-C_6)$alkyl.

In another embodiment, optionally in combination with any of the embodiments provided above or below, A is a known aryl ring comprising 5 or 6 members, wherein one of them is N and the others are —$CR_z$— members, each one of the $R_z$ being independently selected from: H, $(C_1-C_6)$haloalkyl, and halogen. Alternatively, in another embodiment of the invention, optionally in combination with any of the embodiments provided above or below, A represents —NH-A', wherein A' is a known aryl ring comprising 5 or 6 members, wherein one of them is N and the others are —$CR_z$— members, each one of the $R_z$ being independently selected from: H, $(C_1-C_6)$haloalkyl, —O—$(C_1-C_6)$haloalkyl, and halogen.

In one embodiment, optionally in combination with any of the embodiments provided above or below, A is a known aryl ring comprising 5 or 6 members, particularly 6 members, wherein one of them is —N— and the others are —$CR_z$— members, each one of the $R_z$ being independently selected from: H, $(C_1-C_6)$haloalkyl, and halogen. Alternatively, in another embodiment of the invention, optionally in combination with any of the embodiments provided above or below, A represents —NH-A', wherein A' is a known aryl ring comprising 5 or 6 members, particularly 6 members, wherein one of them is —N— and the others are —$CR_2$— members, each one of the $R_z$ being independently selected from: H, $(C_1-C_6)$haloalkyl, —O—$(C_1-C_6)$haloalkyl, and halogen.

Alternatively, in one embodiment, optionally in combination with any of the embodiments provided above or below, A is a known aryl ring comprising 5 or 6 —$CR_z$— members, particularly 6 —$CR_2$— members, each one of the $R_z$ being independently selected from: H, $(C_1-C_6)$haloalkyl, and halogen. Alternatively, in another embodiment of the invention, optionally in combination with any of the embodiments provided above or below, A represents —NH-A', wherein A' is a known aryl ring comprising 5 or 6 —$CR_z$— members, particularly 6 —$CR_2$— members, each one of the $R_z$ being independently selected from: H, $(C_1-C_6)$haloalkyl, —O—$(C_1-C_6)$haloalkyl, and halogen.

In another embodiment, optionally in combination with any of the embodiments provided above or below, $R_1$ is —O—$(C_1-C_{10})$alkyl, $R_2$ is halogen or —$SO_2R_t$, and A represents a known aryl ring comprising 5 or 6 —$CR_2$— members, each one of the $R_z$ being independently selected from: H, $(C_1-C_6)$haloalkyl, and halogen. Alternatively, in another embodiment of the invention optionally in combination with any of the embodiments provided above or below, A represents —NH-A', wherein A' represents a known aryl ring comprising 5 or 6 —$CR_2$— members, each one of the $R_z$ being independently selected from: H, $(C_1-C_6)$haloalkyl, —O—$(C_1-C_6)$haloalkyl, and halogen.

In another embodiment, optionally in combination with any of the embodiments provided above or below, $R_1$ is —O—$(C_1-C_{10})$alkyl, $R_2$ is halogen or —$SO_2R_t$, $R_3$ is —$NH_2$, and A represents a known aryl ring comprising 5 or 6 —$CR_z$— members, each one of the $R_z$ being independently selected from: H, $(C_1-C_6)$haloalkyl, and halogen. Alternatively, in another embodiment of the invention, optionally in combination with any of the embodiments provided above or below, A' represents a known aryl ring comprising 5 or 6 —$CR_z$— members, each one of the $R_z$ being independently selected from: H, $(C_1-C_6)$haloalkyl, —O—$(C_1-C_6)$haloalkyl, and halogen.

In another embodiment, optionally in combination with any of the embodiments provided above or below, $R_1$ is —O—$(C_1-C_{10})$alkyl, $R_2$ is halogen or —$SO_2R_t$, n is 6, and A represents a known aryl ring comprising 5 or 6 —$CR_z$— members, each one of the $R_z$ being independently selected from: H, $(C_1-C_6)$haloalkyl, and halogen. Alternatively, in another embodiment of the invention, optionally in combination with any of the embodiments provided above or below, A' represents a known aryl ring comprising 5 or 6 —$CR_z$— members, each one of the $R_z$ being independently selected from: H, $(C_1-C_6)$haloalkyl, —O—$(C_1-C_6)$haloalkyl, and halogen.

In another embodiment, optionally in combination with any of the embodiments provided above or below, $R_1$ is —O—$(C_1-C_{10})$alkyl, $R_2$ is halogen or —$SO_2R_t$, $R_3$ is —$NH_2$, n is 6, and A represents a known aryl ring comprising 5 or 6 —$CR_z$— members, each one of the $R_z$ being independently selected from: H, $(C_1-C_6)$haloalkyl, and halogen. Alternatively, in another embodiment of the invention, optionally in combination with any of the embodiments provided above or below, A' represents a known aryl ring comprising 5 or 6 —$CR_z$— members, each one of the $R_z$ being independently selected from: H, $(C_1-C_6)$haloalkyl, —O—$(C_1-C_6)$haloalkyl, and halogen.

In another embodiment, the compound of the invention is selected from the group consisting of:

4-amino-5-chloro-2-methoxy-N-((1-morpholinocycloheptyl)methyl)benzamide;

4-amino-5-(ethylsulfonyl)-2-methoxy-N-((1-morpholinocycloheptyl)methyl)benzamide;

4-amino-5-fluoro-2-methoxy-N-((1-morpholinocycloheptyl)methyl)benzamide;

4-amino-2,5-difluoro-N-((1-morpholinocycloheptyl)methyl)benzamide;

6-amino-5-chloro-2-methoxy-N-((1-morpholinocycloheptyl)methyl)nicotinamide;

6-chloro-N-((1-morpholinocycloheptyl)methyl)imidazo[1,2-a]pyridine-8-carboxamide;

N-((1-morpholinocycloheptyl)methyl)quinoxaline-2-carboxamide;

4-amino-5-chloro-2-hydroxy-N-((1-morpholinocycloheptyl)methyl)benzamide;

4-amino-5-chloro-2-methoxy-N-((1-thiomorpholinocycloheptyl)methyl)benzamide;

4-amino-5-chloro-2-methoxy-N-((1-(4-methylpiperazin-1-yl)cycloheptyl)methyl)benzamide;

4-amino-5-chloro-N-((1-(4-fluoropiperidin-1-yl)cyclohexyl)methyl)-2-methoxybenzamide;
4-amino-5-chloro-N-((1-(4,4-difluoropiperidin-1-yl)cyclohexyl)methyl)-2-methoxybenzamide;
4-amino-5-chloro-N-((1-(4-chlorophenyl)cyclopropyl)methyl)-2-methoxybenzamide;
4-amino-5-chloro-N-((1-(4-chlorophenyl)cyclobutyl)methyl)-2-methoxybenzamide;
4-amino-5-chloro-N-((1-(4-chlorophenyl)cyclopentyl)methyl)-2-methoxybenzamide;
4-amino-5-chloro-N-((1-(4-chlorophenyl)cyclohexyl)methyl)-2-methoxybenzamide;
4-amino-5-chloro-N-((1-(4-chlorophenyl)cycloheptyl)methyl)-2-methoxybenzamide;
4-amino-5-chloro-N-((1-((4-chlorophenyl)amino)cycloheptyl)methyl)-2-methoxybenzamide;
4-amino-5-chloro-N-((1-(3,4-dichlorophenyl)cycloheptyl)methyl)-2-methoxybenzamide;
6-amino-5-chloro-N-((1-(4-chlorophenyl)cycloheptyl)methyl)-2-methoxynicotinamide;
5-amino-6-chloro-N-((1-(4-chlorophenyl)cycloheptyl)methyl)chroman-8-carboxamide;
4-amino-5-chloro-N-((1-(4-fluorophenyl)cycloheptyl)methyl)-2-methoxybenzamide;
4-amino-5-chloro-N-((1-(2-chloro-4-fluorophenyl)cycloheptyl)methyl)-2-methoxybenzamide;
4-amino-5-chloro-2-methoxy-N-((1-(4-(trifluoromethyl)phenyl)cycloheptyl)methyl) benzamide;
4-amino-5-chloro-2-methoxy-N-((1-(5-(trifluoromethyl)pyridin-2-yl)cycloheptyl)methyl) benzamide;
4-amino-5-chloro-2-methoxy-N-((1-(pyridin-3-yl)cycloheptyl)methyl)benzamide;
4-amino-5-chloro-N-((1-(2-chloro-4-fluorophenyl)cycloheptyl)methyl)-2-methoxybenzamide;
4-amino-5-chloro-2-methoxy-N-((1-((3-(trifluoromethoxy)phenyl)amino) cycloheptyl)methyl)benzamide;

and any pharmaceutically acceptable salt, hydrate, and isomer thereof.

In another embodiment, the compound of formula (I), which is selected from:

4-amino-5-chloro-2-methoxy-N-((1-thiomorpholinocycloheptyl)methyl)benzamide;
4-amino-5-chloro-N-((1-(4-chlorophenyl)cyclohexyl)methyl)-2-methoxybenzamide;
4-amino-5-chloro-N-((1-(4-chlorophenyl)cycloheptyl)methyl)-2-methoxybenzamide;
4-amino-5-chloro-N-((1-((4-chlorophenyl)amino)cycloheptyl)methyl)-2-methoxybenzamide;
6-amino-5-chloro-N-((1-(4-chlorophenyl)cycloheptyl)methyl)-2-methoxynicotinamide;
4-amino-5-chloro-N-((1-(4-fluorophenyl)cycloheptyl)methyl)-2-methoxybenzamide;
4-amino-5-chloro-N-((1-(2-chloro-4-fluorophenyl)cycloheptyl)methyl)-2-methoxybenzamide;
4-amino-5-chloro-N-((1-(2-chloro-4-fluorophenyl)cycloheptyl)methyl)-2-methoxybenzamide;
4-amino-5-chloro-2-methoxy-N-((1-((3-(trifluoromethoxy)phenyl)amino) cycloheptyl)methyl)benzamide; and any pharmaceutically acceptable salt, hydrate, and isomer thereof.

In a second aspect the present invention provides a process for obtaining the compound of formula (I) as defined above, comprising the reaction between a carboxylic derivative of formula (II) and an amine derivative compound of formula (III) in the presence of a polar solvent, particularly in the presence of a polar aprotic solvent.

The coupling agents to be used in the process of the invention can be any of those already available and used in the formation of amide bonds on the basis of the reaction between a carboxylic group and an amine group (including those already used in the synthesis of peptide amide bonds).

Illustrative non-limitative examples of coupling agents commonly used in amide coupling are: carbodiimides such as dicyclohexylcarbodiimide (DCC), diisopropylcarbodiimide (DIC), 1-ethyl-3-(3-dimethylaminopropyl)carbodiimide (EDC); triazoles 1-hydroxy-benzotriazole (HOBt), and 1-hydroxy-7-aza-benzotriazole (HOAt); cyano derivatives such as ethyl cyanohydroxyiminoacetate (Oxyma); and aminium/uronium reagents such as Hexafluorophosphate Azabenzotriazole Tetramethyl Uronium (HATU, (HOAt)), Hexafluorophosphate Benzotriazole Tetramethyl Uronium/2-(1H-Benzotriazole-1-yl)-1,1,3,3-tetramethylaminium tetrafluoroborate, (HBTU/TBTU (HOBt)), and 2-(6-Chloro-1-H-benzotriazole-1-yl)-1,1,3,3-tetramethylaminium hexafluorophosphate (HCTU (6-ClHOBt)); phosphonium reagents such as (benzotriazol-1-yl-oxytripyrrolidinophosphonium hexafluorophosphate) (PyBOP (HOBt)) and ((7-Azabenzotriazol-1-yloxy)tripyrrolidinophosphonium hexafluorophosphate) (PyAOP (HOAt)); and amine derivatives such as N,N-diisopropylethylamine (DIPEA) or triethylamine. Other known coupling agents can also be found in Albericio F. and collegues (Albericio F. et al., 2018)

Illustrative non-limitative examples of polar aprotic solvents are: dichloromethane (DCM), tetrahydrofuran (THF), ethyl acetate, acetonitrile, dimethylformamide (DMF), and dimethyl sulfoxide (DMSO), among others.

In one embodiment of the second aspect of the invention, optionally in combination with any of the embodiments provided above or below, the reaction is performed in the presence of a polar aprotic solvent together with one or more pair of coupling agents selected from: DIC/HOBt, DIPEA/HATU.

In another embodiment of the process of the second aspect of the invention, optionally in combination with any of the embodiments provided above or below, the reaction is performed in the presence of a polar aprotic solvent, such as dimethylformamide, and the coupling agents DIPEA/HATU.

In another embodiment of the process of the second aspect of the invention, optionally in combination with any of the embodiments provided above or below, the amine compound of formula (III) is in molar excess with respect to the carboxylic compound of formula (II).

In another embodiment of the process of the second aspect of the invention, optionally in combination with any of the embodiments provided above or below, wherein the coupling reaction is performed by sequentially adding the compound of formula (II), the compound of formula (III), and the coupling agent(s).

The compound of formula (II) can be obtained following the protocols already reported in the prior art or are commercially available (by Sigma Aldrich or Alfa Aesar, for example).

The compound of formula (III) can also be obtained following well-known protocols or are commercially available. In one embodiment, the amine compound of formula (III) can be obtained by converting the nitrile group of a compound of formula (IV) into an amine group:

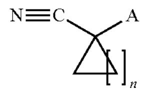

(IV)

wherein A and n are as defined in above.

This conversion can be performed reducing the nitrile group of the compound of formula (IV) into an amine group in the presence of one or more reducing agents. This reduction can optionally be further performed in the presence of a catalyst, such as a Raney-Nickel catalyst.

Depending on the starting cyanide derivative (IV), the skilled person can routinely select the appropriate conditions and reagents to efficiently perform the nitrile reduction. Illustrative non-limitative examples of particular reagents and conditions are provided in the examples below (see section 3 of the "Examples" section, general procedures A to G).

In a third aspect the present invention provides a pharmaceutical composition comprising a therapeutically effective amount of a compound of formula (I), as defined in the first aspect as well as in any of the embodiments of the first aspect of the invention, together with one or more pharmaceutically acceptable excipients or carriers.

The expression "therapeutically effective amount" as used herein, refers to the amount of a compound that, when administered, is sufficient to prevent development of, or alleviate to some extent, one or more of the symptoms of the disease which is addressed. The particular dose of the peptide administered according to this invention will of course be determined by the particular circumstances surrounding the case, including the compound administered, the route of administration, the particular condition being treated, and the similar considerations.

Appropriate amounts of the compound according to the present invention can be formulated with pharmaceutically acceptable excipients and/or carriers to obtain a pharmaceutical composition to be administered in a method for the prevention and/or treatment of an inflammatory condition.

The effective quantity of the compound of the invention can vary within a wide range and, in general, will vary depending on the particular circumstances of application, duration of the exposure and other considerations. Even though individual needs vary, determination of optimal ranges for effective amounts of the compound of the invention belongs to the common experience of those experts in the art. In general, the dosage needed to provide an effective amount of such compound, which can be adjusted by one expert in the art will vary depending on age, health, fitness, sex, diet, weight, degree of alteration of the receptor, frequency of treatment and the nature and extent of impairment or illness, medical condition of the patient, route of administration, pharmacological considerations such as activity, efficacy, pharmacokinetic and toxicology profile of the particular compound used, if using a system drug delivery, and if the compound is administered as part of a combination of drugs.

The expression "pharmaceutically acceptable excipients or carriers" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans and non-human animals without excessive toxicity, irritation, allergic response, immunogenicity or other problems or complications commensurate with a reasonable benefit/risk ratio. Examples of suitable pharmaceutically acceptable excipients are solvents, dispersion media, diluents, or other liquid vehicles, dispersion or suspension aids, surface active agents, isotonic agents, thickening or emulsifying agents, preservatives, solid binders, lubricants and the like. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

A composition that includes the compound according to the invention can be delivered to a subject by a variety of routes including, without limitation, systemically delivery, e.g., by intravenous, subcutaneous or intramuscular injection. Additionally, it is also possible to administer the composition comprising the compound of the invention intranasally which allows systemic administration by a non-aggressive mode of administration. Also, intraventricular administration may be adequate.

Those skilled in the art are familiar with the principles and procedures as a pharmaceutical composition adapted for delivered administration to human beings and other mammals.

Where necessary, the compound of the invention is comprised in a composition also including a solubilizing agent and a local anesthetic to ameliorate any pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided so that the ingredients may be mixed prior to administration.

In cases other than intravenous administration, the composition can contain minor amounts of wetting or emulsifying agents, or pH buffering agents. The composition can be a liquid solution, suspension, emulsion, gel polymer, or sustained release formulation. The composition can be formulated with traditional binders and carriers, as would be known in the art. Formulations can include standard carriers such as pharmaceutical grades of mannitol, lactose, starch, magnesium stearate, sodium saccharide, cellulose, magnesium carbonate, etc., inert carriers having well established functionality in the manufacture of pharmaceuticals. Various delivery systems are known and can be used to administer a therapeutic of the present invention including encapsulation in liposomes, microparticles, microcapsules and the like.

Solid dosage forms for oral administration may include conventional capsules, sustained release capsules, conventional tablets, sustained-release tablets, chewable tablets, sublingual tablets, effervescent tablets, pills, suspensions, powders, granules and gels. At these solid dosage forms, the active compounds can be mixed with at least one inert excipient such as a sucrose, lactose or starch. Such dosage forms can also comprise, as in normal practice, additional substances other than inert diluents, e.g. lubricating agents such as magnesium stearate. In the case of capsules, tablets, effervescent tablets and pills, the dosage forms may also comprise buffering agents. Tablets and pills can be prepared with enteric coatings.

Sustainable-release forms and appropriate materials and methods for their preparation are well-known in the state of the art. In one embodiment of the invention, the orally administrable form of a compound according to the invention is in a sustained release form further comprises at least one coating or matrix. The coating or sustained release matrix include, without limitation, natural polymers, semi-synthetic or synthetic water-insoluble, modified, waxes, fats, fatty alcohols, fatty acids, natural semisynthetic or synthetic plasticizers, or a combination of two or more of them.

Enteric coatings may be applied using conventional processes known to experts in the art.

Injectable preparations, for example, aqueous or oleaginous suspensions, sterile injectable may be formulated according with the technique known using suitable dispersing agents, wetting agents and/or suspending agents. Among the acceptable vehicles and solvents that can be used are water, Ringer's solution and isotonic sodium chloride solution. Sterile oils are also conventionally used as solvents or suspending media.

For topical administration, compounds of the invention can be formulated as creams, gels, lotions, liquids, pomades, spray solutions, dispersions, solid bars, emulsions, microemulsions and similar which may be formulated according to conventional methods that use suitable excipients, such as, for example, emulsifiers, surfactants, thickening agents, coloring agents and combinations of two or more thereof.

Additionally, the compounds of the method of the invention may be administered in the form of transdermal patches or iontophoresis devices. In one embodiment, the compounds of the invention are administered as a transdermal patch, for example, in the form of sustained-release transdermal patch.

In a fifth aspect the present invention provides the use of the compounds of formula (I) in the treatment of an inflammatory condition. All the embodiments provided above, under the first aspect of the invention, regarding the compound of formula (I) are also particular embodiments of the use as defined in the fifth aspect of the invention.

In the context of the invention, term "inflammation", as used herein, is intended to encompass both acute responses (i.e., a response in which the inflammatory processes are active) and chronic responses (i.e., a response marked by slow progress and formation of new connective tissue). Chronic and acute inflammation may be distinguished by the cell types involved. Acute inflammation often involves polymorphonuclear neutrophils; whereas chronic inflammation is normally characterized by a lymphohistiocytic and/or granulomatous response. Examples of specific types of inflammation are diffuse inflammation, focal inflammation, croupous inflammation, interstitial inflammation, obliterative inflammation, reactive inflammation, specific inflammation, toxic inflammation, and traumatic inflammation. The term "inflammation" encompasses both internal inflammation and external inflammation.

In the context of the present invention, the expression "inflammatory condition" refers to either an acute or chronic inflammatory condition characterized by activation of the immune system to abnormal levels that leads to the disease. In particular embodiments, an inflammatory condition is manifested by one or more symptoms selected from the group consisting of redness, heat, swelling (enlargement of any organ or tissue due to accumulation of excessive fluid in said organ or tissue), pain and dysfunction of the tissues or organs involved. All of the five conditions may be observed or associated with an inflammation, but none is necessarily always present. The degree or the severity of the five conditions may vary. For example, the heat, can be localized to the site of inflammation, or it can be systemic, with an increase of several degrees in the body temperature. The dysfunction of the tissues or organs involved can be a partial or a total failure of the tissue or organ. It can range from annoying to life-threatening, depending on severity and on the type of tissue or organ in which the dysfunction occurs.

The inflammatory condition can be associated with, for example, an autoimmune condition, brain inflammation, meningeal inflammation, skin inflammation, inflammatory arthritis, cardiopulmonary inflammation, bladder inflammation, and gastrointestinal inflammation.

Illustrative, non-limiting examples of inflammatory conditions include, but are not limited to, celiac disease, rheumatoid arthritis (RA), inflammatory bowel disease (IBD), asthma, encephalitis, chronic obstructive pulmonary disease (COPD), inflammatory osteolysis, Crohn's disease, ulcerative colitis, allergic disorders, septic shock, pulmonary fibrosis (e.g., idiopathic pulmonary fibrosis), inflammatory vacultides (e.g., polyarteritis nodosa, Wegner's granulomatosis, Takayasu's arteritis, temporal arteritis, and lymphomatoid granulomatosus), post-traumatic vascular angioplasty (e.g. restenosis after angioplasty), undifferentiated spondyloarthropathy, undifferentiated arthropathy, arthritis, inflammatory osteolysis, chronic hepatitis, and chronic inflammation resulting from chronic viral or bacterial infections.

The data presented below support that the compounds of the invention can downregulate the levels of inflammatory chemokines secreted from activated SFs, while exhibiting low cytotoxicity, thus supporting that these compounds may be efficient in affecting the arthritogenic phenotype of activated SFs and consequently may have a therapeutic effect on arthritis.

As SFs have been demonstrated to be the cellular drivers of arthritic pathologies, the effect of the test compounds on activated SFs provides supporting evidence that these test compounds could be used as an alternative effective small molecule treatment for the therapy of arthritis.

The results of this analysis show that the different test compounds may remarkably affect the proliferative and migratory capacity of activated SFs and may thus have a therapeutic effect in diseases where SFs play a major pathogenic role as is the case of arthritis.

Thus, in one embodiment, the inflammation condition is arthritis.

Arthritis manifests itself in a variety of forms. Some of the more common forms include rheumatoid arthritis, osteoarthritis and generalized rheumatism.

Rheumatoid arthritis is an autoimmune disease characterized by pain, swelling and stiffness in the joints. Osteoarthritis produces similar symptoms to rheumatoid arthritis. In particular, although osteoarthritis begins as a degeneration of articular cartilage whereas rheumatoid arthritis begins as inflammation in the synovium, each process approaches the other as the disease progresses. In osteoarthritis, as cartilage deteriorates and joint congruence is altered, a reactive synovitis often develops. Conversely, as rheumatoid arthritis erodes cartilage, secondary osteoarthritis changes in bone and cartilage develop. At the end stages of both osteoarthritis and rheumatoid arthritis, the involved joints appear the same. Some other forms of arthritis include Ankylosing Seronegative Spondyloarthropathy (ankylosing spondylitis) and reactive arthritis. These conditions are often referred to as the "B-27 associated diseases," and are difficult to differentiate from rheumatoid arthritis. In some cases ankylosing spondylitis, Reiters syndrome or psoriatic arthritis are present coincidingly with Rheumatoid Arthritis in the same patient.

In one embodiment, the inflammatory condition is rheumatoid arthritis.

In another embodiment of the fifth aspect of the invention, optionally in combination with any of the embodiments provided above or below, the compound of formula (I) is administered in combination with a further drug selected from anti-inflammatory agent, analgesic or anti-pyretic agents. In one embodiment of the fifth aspect of the invention, optionally in combination with any of the embodiments provided above or below, the compound of formula (I) is administered simultaneously, sequentially or separately from the further anti-inflammatory agent.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

EXAMPLES

Synthesis of the Compounds of the Invention

1. Synthesis of the Acid Compounds of Formula (II):

The acid compounds of formula (II) were synthesized following previous publications or purchased from manufacturer's companies. The following Table 1 summarizes the acid compounds used in the synthesis of the exemplified compounds of the invention as well as the source for its obtaining:

TABLE 1

| Compound of formula (II) | Source |
| --- | --- |
| 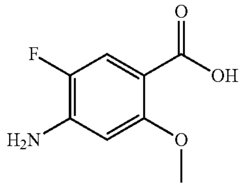 (62) | Synthesized according to Estrada AA et al., *J. Med. Chem.*, 2012, 55, 9416-9433 |
| 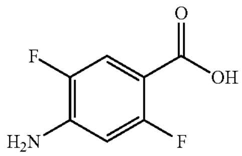 (63) | Synthesized according to Matikonda SS et al., *Bioconj. Chem.*, 2018, 29, 324-334 |
| 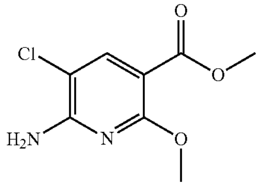 (64) | Synthesized according to WO2006/112828 A1, page 59, paragraph [0167] |

TABLE 1-continued

| Compound of formula (II) | Source |
| --- | --- |
| 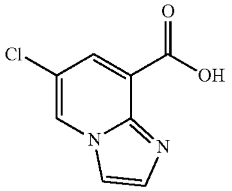 (65) | Synthesized according to Becker DP et al., *J. Med. Chem.*, 2006, 49, 1125-1139 |
| 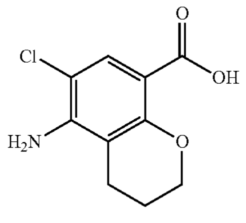 (66) | Synthesized according to Rassias G. et al., *Org. Proc. Res. Dev.*, 2010, 14, 92-98. |
| 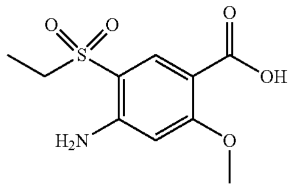 (67) | Synthesized according to US2013/0096319A1, page 12, compound IV |
| 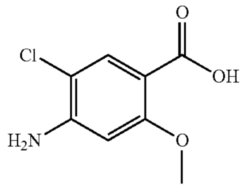 (68) | Purchased by Alfa Aesar |
| 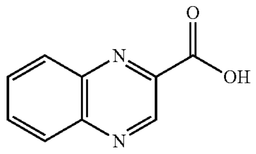 (69) | Purchased by Alfa Aesar |

2. Synthesis of the Amine Compounds of Formula (III)

The obtaining of the compounds of formula (III) is based on the conversion of the —CN group of a cyanide compound of formula (IV) into an —$NH_2$:

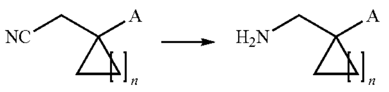

(IV) (III)

2.1. Synthesis of the Cyanide Compounds of Formula (IV)

2.1.1. Synthesis of 1-(piperidin-1-yl)cycloheptanecarbonitrile (1)

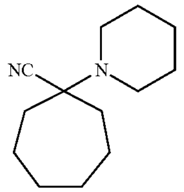 [SMILES: N#CC1(N2CCCCC2)CCCCCC1]

Aceton cyanohydrine (1 eq.) and piperidine (2 eq.) were added to a suspension of $MgSO_4$ (3 eq.) and cycloheptanone (1 eq.) in 5 mL anhydrous N,N-dimethylacetamide ("DMAc") under Ar at room temperature ("rt"). The mixture was stirred at 55° C. for 72 h, quenched with $H_2O$, and extracted with ethyl acetate ("EtOAc"). The combined organic layers were washed with $H_2O$ and brine, dried over $Na_2SO_4$, filtered and concentrated under reduced pressure. Purification of the compound was performed by column chromatography eluted with different proportions of hexane: EtOAc 95:5 to 90:10. It was obtained a pale yellow oil. MS: (M+1)=207.2.

2.1.2. Synthesis of 1-thiomorpholinocycloheptanecarbonitrile (2)

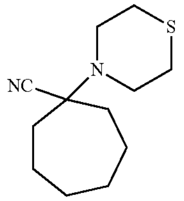 [SMILES: N#CC1(N2CCSCC2)CCCCCC1]

Thiomorpholine (2.2 eq.) in THF was added to a mixture of cycloheptanone (1 eq.) and diethyl phosphorocyanidate (1.2 eq.) in 10 mL dry tetrahydrofuran ("THF") and the resulting mixture was stirred at reflux until completion of the reaction. The mixture was concentrated in vacuum and purified by column chromatography eluted with hexane: EtOAc 95:5. It was obtained as a pale yellow oil. MS: (M+1)=225.1

2.1.3. Synthesis of Tert-Butyl 4-(1-Cyanocycloheptyl)Piperazine-1-Carboxylate (3)

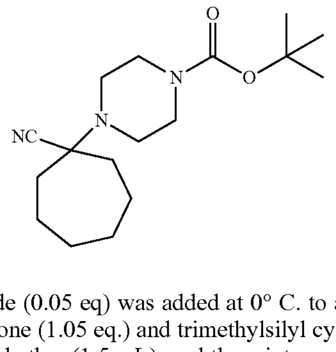

Zinc iodide (0.05 eq) was added at 0° C. to a solution of cycloheptanone (1.05 eq.) and trimethylsilyl cyanide (1 eq.) in dry diethyl ether (1.5 mL), and the mixture was stirred at the same temperature for 30 min. To the solution was added dropwise 1-Boc-piperazine (1 eq.) dissolved in MeOH (9 mL) at rt and the mixture was heated at reflux for 4h and at rt overnight. The reaction mixture was then concentrated in vacuum and purified by column chromatography eluted with hexane:EtOAc 95:5. It was obtained as a pale yellow oil. MS: (M+1)=308.2

2.1.4. Synthesis of 1-(4-fluoropiperidin-1-yl)cyclohexanecarbonitrile (4)

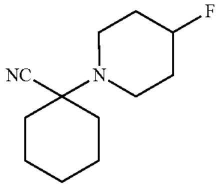 [SMILES: N#CC1(N2CCC(F)CC2)CCCCC1]

4-fluoropiperidine (1.10 eq) and potassium cyanide (1.05 eq.) were added to a solution of the for 24 h. The mixture was extracted with ethyl acetate, the organic phase was washed with brine, dried, filtered and concentrated in vacuum. The product was used in the next step without further purification. It was obtained a pale yellow oil. MS: (M+1)=211.4.

2.1.5. Synthesis of 1-(4,4-difluoropiperidin-1-yl)cyclohexanecarbonitrile (5)

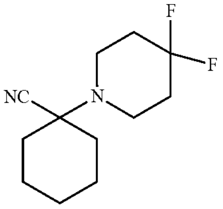 [SMILES: N#CC1(N2CCC(F)(F)CC2)CCCCC1]

4,4-difluoropiperidine (1.10 eq) and potassium cyanide (1.05 eq.) were added to a solution of cyclohexanone (1.0 eq.) in MeOH:$H_2O$ (1:1) and the resulting mixture was stirred at rt for 24 h. The mixture was extracted with ethyl acetate, the organic phase was washed with brine, dried, filtered and concentrated in vacuum. The product was used in the next step without further purification. It was obtained a pale yellow oil. MS: (M+1)=229.2

2.1.6. Synthesis of 1-((4-chlorophenyl)amino)cycloheptanecarbonitrile (6)

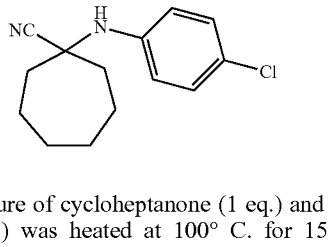

A neat mixture of cycloheptanone (1 eq.) and 4-chloroaniline (1.3 eq.) was heated at 100° C. for 15 min. The mixture was then cooled to rt, trimethylsilyl cyanide (1.3 eq.) was added and the mixture was heated at 100° C. for 15 min. The mixture was cooled down to rt, ethyl acetate was added, the organic phase was washed with $H_2O$ and brine, dried, filtered and concentrated in vacuum. Cold hexane was added to the residue and the solid formed was filtered, washed with cold hexane and dried. It was obtained as a white solid. MS: (M+1)=250.1

2.1.7. Synthesis of 1-((2-chloro-4-fluorophenyl)amino)cycloheptane-1-carbonitrile (a)

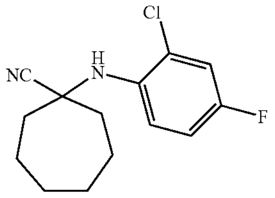 [SMILES: N#CC1(Nc2ccc(F)cc2Cl)CCCCCC1]

A mixture of cycloheptanone (1 eq.) and 2-chloro-4-fluoroaniline (1.3 eq.) was stirred at 0° C. while trimethylsilyl cyanide (1.3 eq.) was added. The mixture was stirred overnight at room temperature. 5% aqueous solution of sodium bicarbonate was added, the mixture was extracted with ethyl acetate, the combined organic phase was washed with brine, dried, filtered and concentrated in vacuum. The residue was purified by plash chromatography eluted with hexane:ethyl acetate 2:1. It was obtained as a white solid. MS: (M+1)=267.7.

2.1.8. Synthesis of 1-((3-(trifluoromethoxy)phenyl)amino)cycloheptane-1-carbonitrile (b)

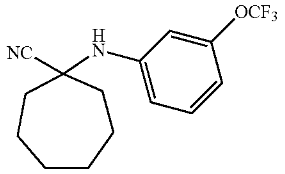 [SMILES: N#CC1(Nc2cccc(OC(F)(F)F)c2)CCCCCC1]

The same procedure as in previous section 2.1.7 was followed but replacing 2-chloro-4-fluoroaniline with 3-trifluoromethoxyaniline. MS: (M+1)=299.1.

2.1.9. Synthesis of Cyanide Compounds (14) to (24)

To a suspension of sodium hydride, NaH (60% oil dispersion, 2.2 eq.) in dimethylsulfoxide ("DMSO")/THF 1:1 (12 mL solvent/mmol phenyl acetonitrile derivative) was added dropwise a mixture of the phenyl acetonitrile derivative (1 eq.) and 1.1 eq of the respective dibromide analogue (1,2-dibromoethane, 1,3-dibromopropane, 1,4-dibromobutane, 1,5-dibromopentane, and 1,6-dibromohexane) under Ar. On completion of the addition, the mixture was stirred at rt and under Ar overnight. The reaction was quenched with $H_2O$, extracted with EtOAc, the organic phase was washed with $H_2O$ and brine, dried over $Na_2SO_4$, filtered and concentrated in vacuum. The residue was purified by column chromatography eluted with different proportions of hexane: EtOAc 98:2 to 98:5.

TABLE 2a

| Compound | | Acetonitrile derivative/dibromide analogue |
|---|---|---|
| (14) | 1-(4-chlorophenyl)cyclopropane carbonitrile 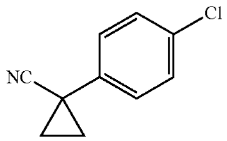 | 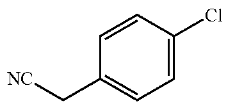 + 1,2-dibromoethane |

TABLE 2a-continued

| Compound | | Acetonitrile derivative/dibromide analogue |
|---|---|---|
| (15) | 1-(4-chlorophenyl)cyclobutane carbonitrile 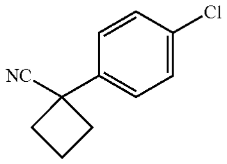 | 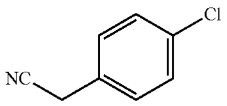 + 1,3-dibromopropane |
| (16) | 1-(4-chlorophenyl)cyclopentane carbonitrile 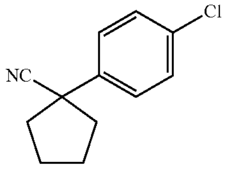 | 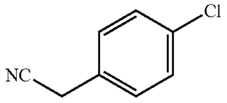 + 1,4-dibromobuthane |
| (17) | 1-(4-chlorophenyl)cyclohexane carbonitrile 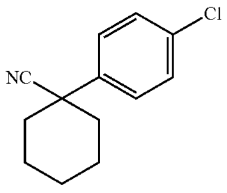 | 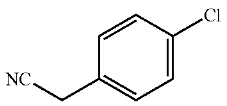 + 1,5-dibromopentane |
| (18) | 1-(4-chlorophenyl)cycloheptane Carbonitrile 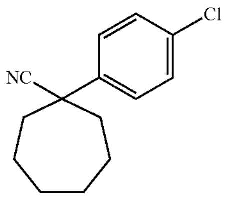 | 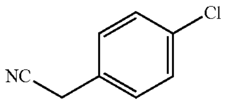 + 1,6-dibromohexane |
| (19) | 1-(3,4-dichlorophenyl)cycloheptane carbonitrile 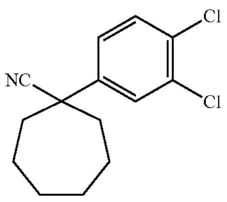 | 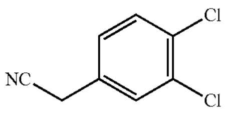 + 1,6-dibromohexane |

TABLE 2a-continued

| Compound | | Acetonitrile derivative/dibromide analogue |
|---|---|---|
| (20) | 1-(4-fluorophenyl)cycloheptane carbonitrile 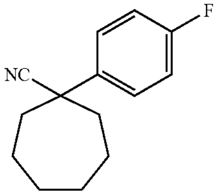 | 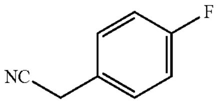 + 1,6-dibromohexane |
| (21) | 1-(2-chloro-4-fluorophenyl)cycloheptanecarbonitrile 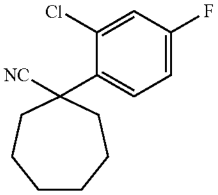 | 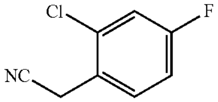 + 1,6-dibromohexane |
| (22) | 1-(4-(trifluoromethyl)phenyl) cycloheptanecarbonitrile 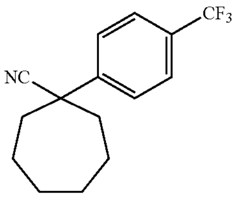 | 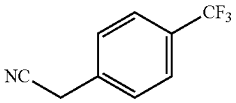 + 1,6-dibromohexane |
| (23) | 1-(pyridin-3-yl)cycloheptane carbonitrile 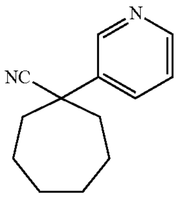 | 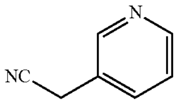 + 1,6-dibromohexane |
| (24) | 1-(5-(trifluoromethyl)pyridin-2-yl)cycloheptanecarbonitrile 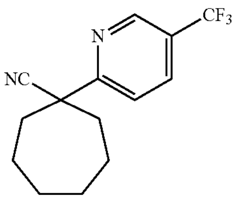 | 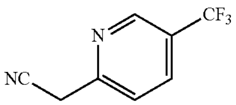 + 1,6-dibromohexane |

TABLE 2b

| | Compound | Properties |
|---|---|---|
| (14) | 1-(4-chlorophenyl)cyclopropane carbonitrile 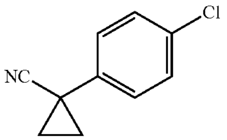 | Pale yellow oil. MS: (M + 1) = 179.0 |
| (15) | 1-(4-chlorophenyl)cyclobutane carbonitrile 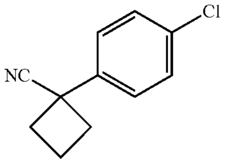 | Pale yellow oil. MS: (M + 1) = 193.1 |
| (16) | 1-(4-chlorophenyl)cyclopentane carbonitrile 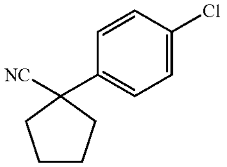 | Pale yellow oil. MS: (M + 1) = 207.1 |
| (17) | 1-(4-chlorophenyl)cyclohexane carbonitrile 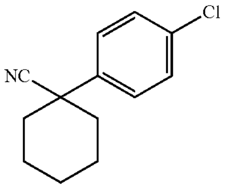 | Pale yellow oil. MS: (M + 1) = 221.1 |
| (18) | 1-(4-chlorophenyl)cycloheptane carbonitrile 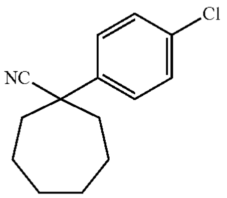 | Pale yellow oil. MS: (M + 1) = 235.1 |
| (19) | 1-(3.4-dichlorophenyl)cycloheptanecarbonitrile 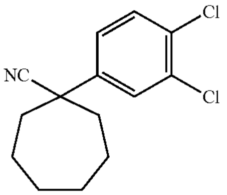 | Pale yellow oil. MS: (M + 1) = 269.1 |

TABLE 2b-continued

| | Compound | Properties |
|---|---|---|
| (20) | 1-(4-fluorophenyl)cycloheptane carbonitrile 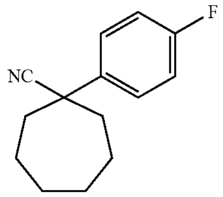 | Pale yellow oil. MS: (M + 1) = 218.1 |
| (21) | 1-(2-chloro-4-fluorophenyl)cycloheptanecar bonitrile 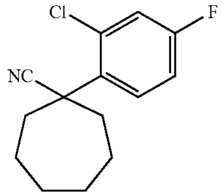 | Pale yellow oil. MS: (M + 1) = 253.1 |
| (22) | 1-(4-(trifluoromethyl)phenyl) cycloheptanecarbonitrile 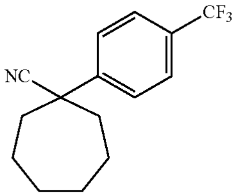 | Pale yellow oil. MS: (M+ 1) = 268.1 |
| (23) | 1-(phridin-3-yl)cycloheptane carbonitrile 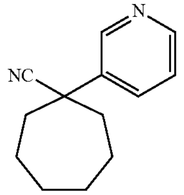 | Brownish oil. MS: (M+ 1) = 201.0 |
| (24) | 1-(5-(trifluoromethyl)pyridin-2-yl)cycloheptanecarbonitrile 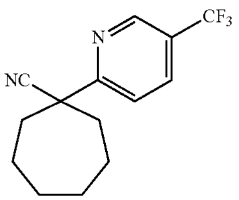 | Pale yellow oil. MS: (M+ 1) = 269.1 |

2.2. Synthesis of the Amine Compounds of Formula (III) from the Cyanide Compounds of Formula (IV)

In order to perform this synthesis, several approaches were made:

General procedure A: To a solution of lithium aluminum hydride (3.2 eq.) in tetrahydrofuran (3 mL) in a round bottom flask at 0° C. was added a solution of sulfuric acid (1.25 eq.) in tetrahydrofuran (1 mL). The mixture was stirred at 0° C. for 1 h then allowed to warm to room temperature and stirred overnight. The mixture was cooled back down to 0° C. and a solution of the compound of formula (1) (1 eq.) in tetrahydrofuran (2 mL) was added dropwise. The reaction was then heated to 50° C. for 1.5 h, cooled and added to a saturated solution of sodium sulfate. Ether was then added and the mixture stirred for 3 h. The layers were then separated and the aqueous layer extracted one more time with diethyl ether. The organic layers were combined, dried (sodium sulfate) and evaporated. The crude material was used in the next step without further purification.

General procedure B: To a solution of lithium aluminum hydride (2-4 eq.) in tetrahydrofuran or diethyl ether (5 mL) in a round bottom flask at 0° C. was added the compounds of formula (3), (4), (5), (a) or (b) (1 eq.), and the mixture was stirred at rt for 1-24 h. The mixture was quenched with EtOAc and 2M aq. $Na_2CO_3$ solution. The layers were separated, the aqueous layer was extracted with EtOAc, the combined organic layers were washed with $H_2O$ and brine, dried over $Na_2SO_4$, filtered and concentrated in vacuum. The crude material was used in the next step without further purification.

General procedure C: An oven-dried vial equipped with a stir bar was charged with compound (2), (23) or (24) (1 eq.), placed under a positive pressure of argon, and subjected to three evacuation/backfilling cycles under high vacuum. Samarium(II) iodide (0.5 MTHF solution, 6 eq.) was added followed by $Et_3N$ (6 eq.) and $H_2O$ (6 eq.) with vigorous stirring, which resulted in the formation of a characteristic dark brown color of the $SmI_2$-$Et_3N$—$H_2O$ complex, and the reaction mixture was stirred for 3 h. The excess of Sm(II) was oxidized by bubbling air through the reaction mixture, and the reaction mixture was diluted with $CH_2Cl_2$ and 1N NaOH. The aqueous layer was extracted with $CH_2Cl_2$ (3×20 mL), the organic layers were combined, washed with $Na_2S_2O_3$ (5 mL, aq., sat.), dried over $Na_2SO_4$, filtered, and concentrated. The crude material was used in the next step without further purification.

General procedure D: To a solution of a compounds of formula (20), (21) or (22) in EtOH (1.5 mL), was added a 25% aqueous solution of $NH_3$ (2.5 eq.) and Ra—Ni catalyst (1.50 eq.) under Ar. The reaction mixture was then stirred at rt under atmosphere of $H_2$ (1 atm) overnight. The catalyst was filtered, washed with EtOH and the filtrate was concentrated in vaccum. The crude material was used in the next step without further purification.

General Procedure E: To a solution of lithium aluminum hydride (2 eq.) in tetrahydrofuran (10 mL) in a round bottom flask at 0° C. was added compounds of formula (14), (15) or (16) (1 eq.), and the mixture was stirred at rt overnight. The mixture was quenched with EtOAc and 2M aq. $Na_2CO_3$ solution. The layers were separated, the aqueous layer was extracted with EtOAc, the combined organic layers were washed with $H_2O$ and brine, dried over $Na_2SO_4$, filtered and concentrated in vacuum. The crude material was used in the next step without further purification.

General Procedure F: To a 1 M solution of $BH_3$: THF complex (10 eq.) was added dropwise a solution of a compound (17), (18) or (19) (1 eq.) in THF (3 mL) at rt. The mixture was then refluxed overnight, acidified at rt with an aqueous 2M solution of HCl until pH 12 and refluxed for further 30 min. THF was removed in vacuum, the aqueous phase was washed with diethyl ether and the aqueous phase was basified with 1M NaOH until pH 12. It was then extracted with EIOAc and concentrated in vacuum. The crude material was used in the next step without further purification.

Thus, the amine compounds listed in Table 3 below were synthesized. The mass spectroscopy (API 2000 mass spectrometer) was determined for each one of the final crude materials:

TABLE 3

| Amine compound of formula (III) | Information |
|---|---|
| (1-(piperidin-1-yl)cycloheptyl)methanamine (7) 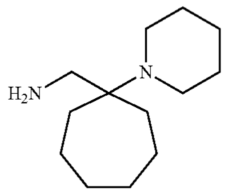 | The general procedure A was followed using compound (1) as starting material. Brown solid. MS: (M + 1) = 211.2 |
| (1-thiomorpholinocycloheptyl)methanamine (9) 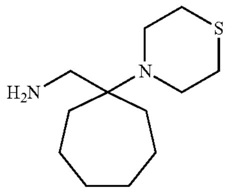 | The general procedure C was followed using compound (2) as starting material. Yellow oil. MS: (M + 1) = 229.2 |
| (1-(4-methylpiperazin-1-yl)cycloheptyl)methanamine (10) 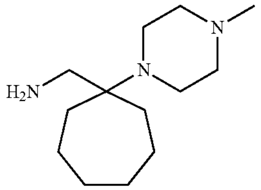 | The general procedure B was followed using compound (3) as starting material. White solid. MS: (M + 1) = 226.2 |
| (1-(4-fluoropiperidin-1-yl)cyclohexyl)methanamine (11) 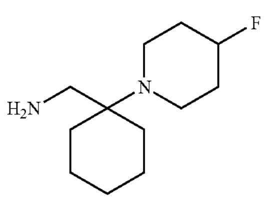 | The general procedure B was followed using compound (4) as starting material. Brown solid. MS: (M + 1) = 229.2 |
| (1-(4,4-difluoropiperidin-1-yl)cyclohexyl)methanamine (12) 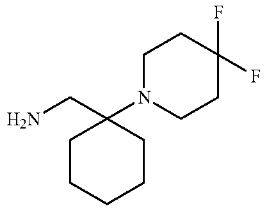 | The general procedure B was followed using compound (5) as starting material. MS: (M + 1) = 233.2 |

TABLE 3-continued

| Amine compound of formula (III) | Information |
|---|---|
| 1-(aminomethyl)-N-(4-chlorophenyl)cycloheptanamine (13) 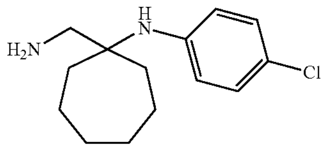 | The general procedure B was followed using compound (6) as starting material. MS: (M + 1) = 253.1 |
| 1-(aminomethyl)-N-(2-chloro-4-fluorophenyl)cycloheptan-1-amine (c) 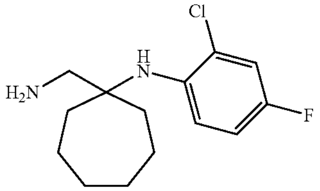 | The general procedure B was followed using compound (a) as starting material. MS: (M + 1) = 271.8 |
| 1-(aminomethyl)-N-(3-(trifluoromethoxy)phenyl)cycloheptan-1-amine (d) 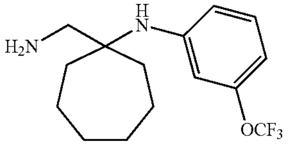 | The general procedure B was followed using compound (b) as starting material. MS: (M + 1) = 303.3 |
| (1-(4-chlorophenyl)cyclopropyl)methanamine (25) 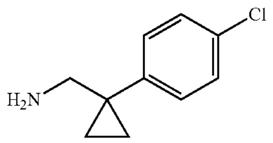 | The general procedure E was followed using compound (14) as starting material. Yellow oil. MS: (M + 1) = 183.1 |
| (1-(4-chlorophenyl)cyclobutyl)methanamine (26) 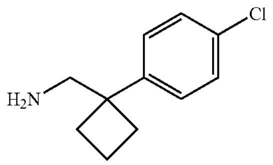 | The general procedure E was followed using compound (15) as starting material. Yellow oil. MS: (M + 1) = 197.1 |
| (1-(4-chlorophenyl)cyclopentyl)methanamine (27) 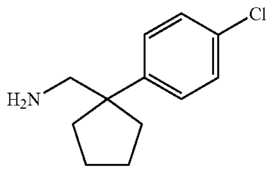 | The general procedure E was followed using compound (16) as starting material. Yellow oil. MS: (M + 1) = 211.1 |

TABLE 3-continued

| Amine compound of formula (III) | Information |
|---|---|
| (1-(4-chlorophenyl)cyclohexyl)methanamine (28) 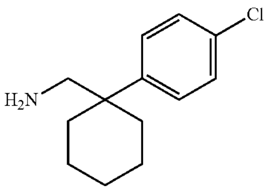 | The general procedure F was followed using compound (17) as starting material. Yellow oil. MS: (M + 1) = 225.1 |
| (1-(4-chlorophenyl)cycloheptyl)methanamine (29) 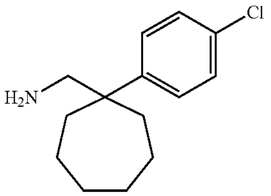 | The general procedure F was followed using compound (18) as starting material. Yellow oil. MS: (M + 1) = 239.1 |
| (1-(3,4-dichlorophenyl)cycloheptyl) methanamine (30) 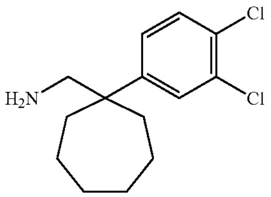 | The general procedure F was followed using compound (19) as starting material. Yellow oil. MS: (M + 1) = 273.1 |
| (1-(4-fluorophenyl)cycloheptyl)methanamine (31) 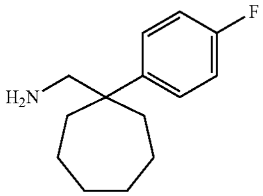 | The general procedure D was followed using compound (20) as starting material. Yellow oil. MS: (M + 1) = 222.2 |
| (1-(2-chloro-4-fluorophenyl)cycloheptyl)methanamine (32) 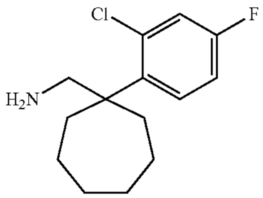 | The general procedure D was followed using compound (21) as starting material. Yellow oil. MS: (M + 1) = 257.0 |
| (1-(4-(trifluoromethyl)phenyl)cycloheptyl) methanamine (33) 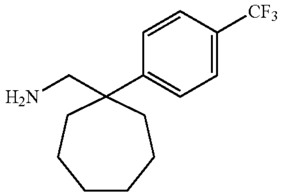 | The general procedure D was followed using compound (22) as starting material. Yellow oil. MS: (M + 1) = 272.2 |
| (1-(pyridin-3-yl)cycloheptyl)methanamine (34) 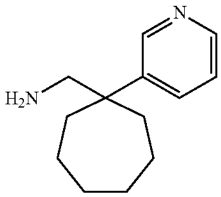 | The general procedure C was followed using compound (23) as starting material. Yellow oil. MS: (M + 1) = 205.2 |
| (1-(5-(trifluoromethyl)pyridin-2-yl)cycloheptyl)methanamine (35) 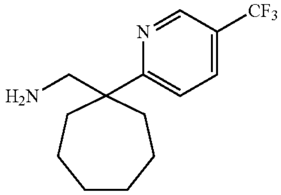 | The general procedure C was followed using compound (24) as starting material. Yellow oil. MS: (M + 1) = 273.1 |

(1-morpholinocycloheptyl)methanamine (8)

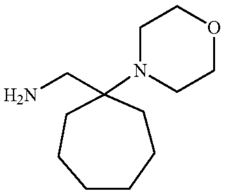 [SMILES: NCC1(N2CCOCC2)CCCCCC1]

was purchased from SIGMA-ALDRICH.

3. Protocol for Obtaining the Compounds of Formula (1) of the Invention

The general procedure was the following:

The acid of formula (II) (1 eq.) was dissolved in dry DMF (1.5 mL) and then the corresponding amine of formula (III) (1.2 eq.), dissolved in DMF (1.5 mL), DIPEA (2.5 eq) and HATU (1.20 eq) were added in order. Then the reaction mixture was stirred at room temperature overnight. $H_2O$ (10 mL) was added, the resulting suspension was extracted with EtOAc (3×20 mL), the combined organic phase was washed with $H_2O$ (10 mL) and brine (10 mL), dried over $Na_2SO_4$, filtered and concentrated in vacuum. The residue was purified by column chromatography eluted with hexane:EtOAc (3:1 to 1:1). The yield was determined in terms of percentage by weight.

The compounds of formula (I) thus obtained were characterized by $^1$H-NMR (Bruker Avance DRX 400 MHZ) and Mass Spectroscopy (API 2000 mass spectrometer).

The following Table 4 summarizes the acid of formula (II), the amine of formula (III) and the compound of formula (I) obtained following the above protocol:

TABLE 4

| Acid of formula (II) | Amine of formula (III) | Compound of formula (I) |
|---|---|---|
| (68) | (8) | 4-amino-5-chloro-2-methoxy-N-((1-morpholinocycloheptyl)methyl)benzamide (36) 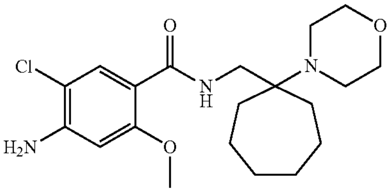 |
| (67) | (8) | 4-amino-5-(ethylsulfonyl)-2-methoxy-N-((1-morpholinocycloheptyl)methyl)benzamide (37) 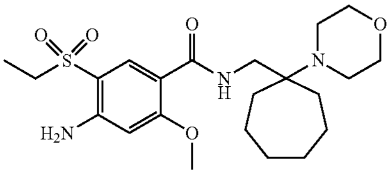 |
| (62) | (8) | 4-amino-5-fluoro-2-methoxy-N-((1-morpholinocycloheptyl)methyl)benzamide (38) 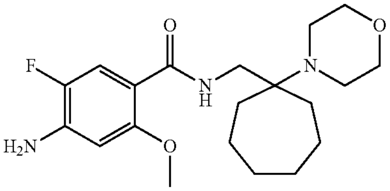 |
| (63) | (8) | 4-amino-2,5-difluoro-N-((1-morpholinocycloheptyl)methyl)benzamide (39) 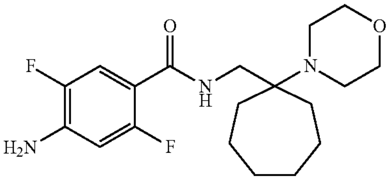 |
| (68) | (8) | 6-amino-5-chloro-2-methoxy-N-((1-morpholinocycloheptyl)methyl)nicotinamide (40) 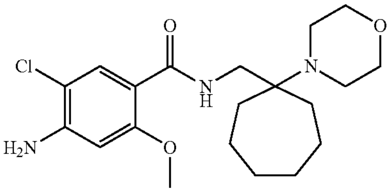 |

TABLE 4-continued

| Acid of formula (II) | Amine of formula (III) | Compound of formula (I) |
|---|---|---|
| (65) | (8) | 6-chloro-N-((1-morpholinocycloheptyl)methyl)imidazo[1,2-a]pyridine-8-carboxamide (41) 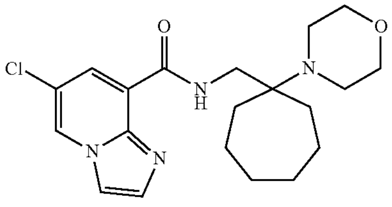 |
| (69) | (8) | N-((1-morpholinocycloheptyl)methyl) quinoxaline-2-carboxamide (42) 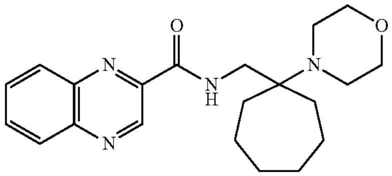 |
| (68) | (9) | 4-amino-5-chloro-2-methoxy-N-((1-thiomorpholinocycloheptyl)methyl)benzamide (44) 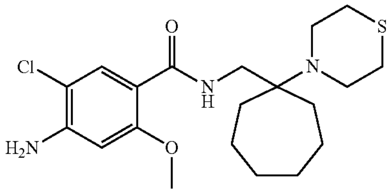 |
| (68) | (10) | 4-amino-5-chloro-2-methoxy-N-((1-(4-methylpiperazin-1-yl)cycloheptyl)methyl)benzamide (45) 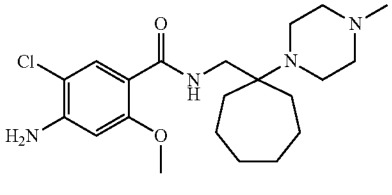 |
| (68) | (11) | 4-amino-5-chloro-N-((1-(4-fluoropiperidin-1-yl)cyclohexyl)methyl)-2-methoxybenzamide (46) 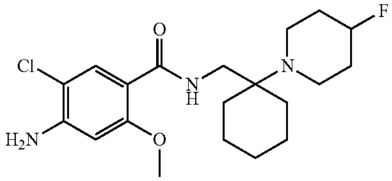 |

TABLE 4-continued

| Acid of formula (II) | Amine of formula (III) | Compound of formula (I) |
|---|---|---|
| (68) | (12) | 4-amino-5-chloro-N-((1-(4,4-difluoropiperidin-1-yl)cyclohexyl)methyl)-2-methoxybenzamide (47) 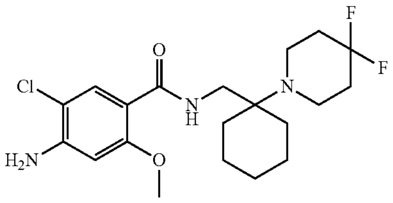 |
| (68) | (25) | 4-amino-5-chloro-N-((1-(4-chlorophenyl)cyclopropyl)methyl)-2-methoxybenzamide (48) 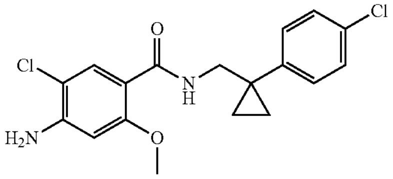 |
| (68) | (26) | 4-amino-5-chloro-N-((1-(4-chlorophenyl)cyclobutyl) methyl)-2-methoxybenzamide (49) 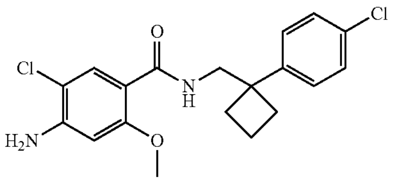 |
| (68) | (27) | 4-amino-5-chloro-N-((1-(4-chlorophenyl)cyclopentyl)methyl)-2-methoxybenzamide (50) 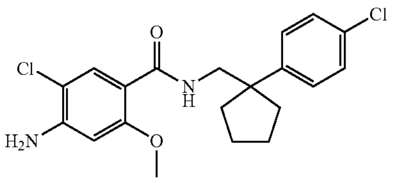 |
| (68) | (28) | 4-amino-5-chloro-N-((1-(4-chlorophenyl)cyclohexyl)methyl)-2-methoxybenzamide (51) 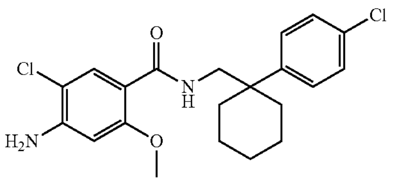 |

TABLE 4-continued

| Acid of formula (II) | Amine of formula (III) | Compound of formula (I) |
|---|---|---|
| (68) | (29) | 4-amino-5-chloro-N-((1-(4-chlorophenyl)cycloheptyl)methyl)-2-methoxybenzamide (52) 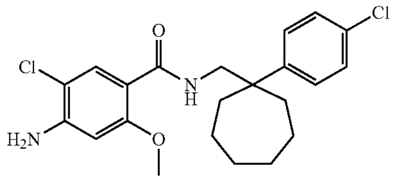 |
| (68) | (13) | 4-amino-5-chloro-N-((1-((4-chlorophenyl)amino)cycloheptyl)methyl)-2-methoxybenzamide (53) 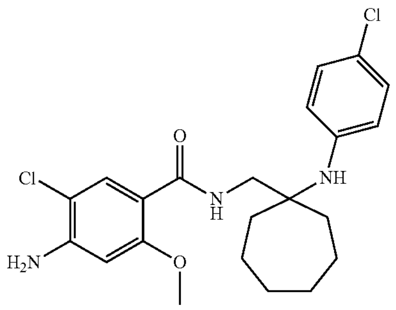 |
| (68) | (13) | 4-amino-5-chloro-N-((1-(3,4-dichlorophenyl)cycloheptyl)methyl)-2-methoxybenzamide (54) 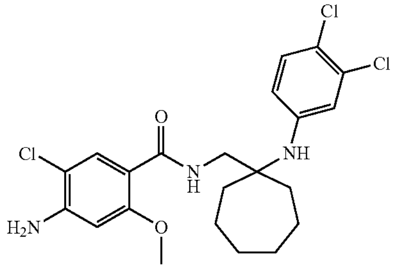 |
| (68) | (c) | 4-amino-5-chloro-N-((1-((2-chloro-4-fluorophenyl)amino)cycloheptyl)methyl)-2-methoxybenzamide (E) 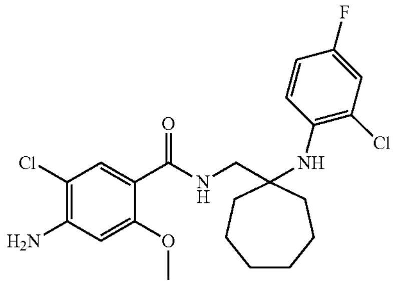 |

TABLE 4-continued

| Acid of formula (II) | Amine of formula (III) | Compound of formula (I) |
|---|---|---|
| (68) | (d) | 4-amino-5-chloro-2-methoxy-N-((1-((3-(trifluoromethoxy)phenyl)amino)cycloheptyl) methyl)benzamide (F) 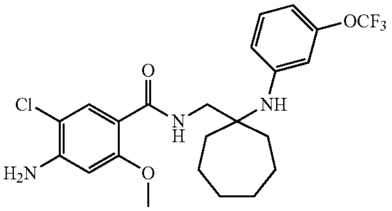 |
| (68) | (29) | 6-amino-5-chloro-N-((1-(4-chlorophenyl)cycloheptyl)methyl)-2-methoxynicotinamide (55) 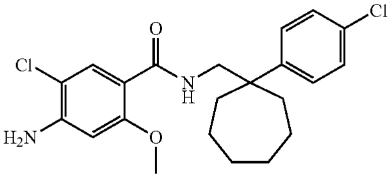 |
| (66) | (29) | 5-amino-6-chloro-N-((1-(4-chlorophenyl)cycloheptyl)methyl)chroman-8-carboxamide (56) 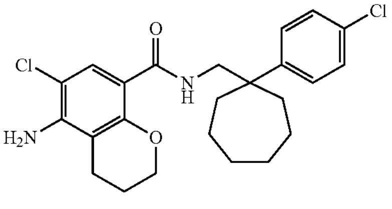 |
| (68) | (31) | 4-amino-5-chloro-N-((1-(4-fluorophenyl)cycloheptyl)methyl)-2-methoxybenzamide (57) 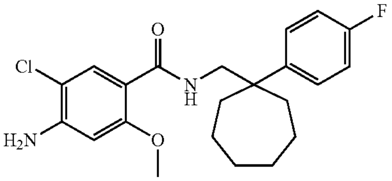 |
| (68) | (32) | 4-amino-5-chloro-N-((1-(2-chloro-4-fluorophenyl)cycloheptyl)methyl)-2-methoxybenzamide (58) 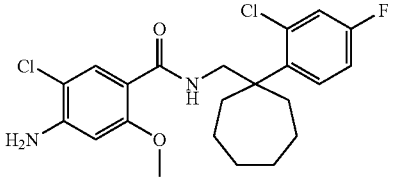 |
| (68) | (35) | 4-amino-5-chloro-2-methoxy-N-((1-(4-(trifluoromethyl)phenyl)cycloheptyl)methyl) benzamide (59) 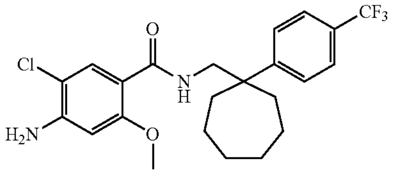 |
| (68) | (35) | 4-amino-5-chloro-2-methoxy-N-((1-(5-(trifluoromethyl)pyridin-2-yl)cycloheptyl)methyl)benzamide (60) 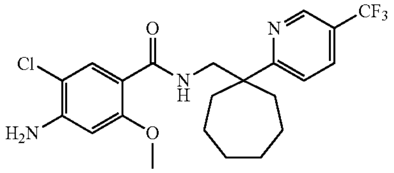 |
| (68) | (34) | 4-amino-5-chloro-2-methoxy-N-((1-(pyridin-3-yl)cycloheptyl)methyl)benzamide (61) 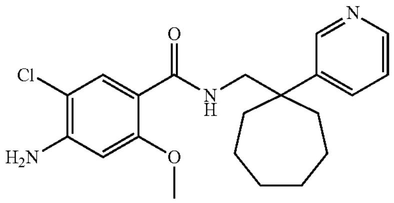 |

The following Table 5 summarizes for each one of the compounds of formula (I), the appearance, yield (% wt), $H^1$ NMR (DMSO-$d_6$) and mass:

TABLE 5

| Compound of formula (I) | yield (% wt) and the $H^1$ NMR (DMSO-$d_6$ or $CDCl_3$): |
|---|---|
| 4-amino-5-chloro-2-methoxy-N-((1-morpholinocycloheptyl)methyl)benzamide (36) | White solid. Yield = 55%. $H^1$ NMR (DMSO-$d_6$): 1.34-1.58 (m, 10H), 1.72-1.78 (m, 2H), 2.50-2.52 (m, 4H), 3.30 (m, 2H), 3.58 (m, 4H), 3.89 (s, 3 H), 5.96 (s, 2H), 6.50 (s, 1H), 7.73 (s, 1H), 8.11 (s, 1H). MS: (M + 1) = 397.1 |
| 4-amino-5-(ethylsulfonyl)-2-methoxy-N-((1-morpholinocycloheptyl)methyl) benzamide (37) | White solid. Yield = 50%. $H^1$ NMR (DMSO-$d_6$): 1.08 (t, J = 7.3 Hz, 3H), 1.35-1.51 (m, 10H), 1.73-1.79 (m, 2H), 2.50-2.52 (m, 4H), 3.15 (q, J = 7.3 Hz, 2H), 3.31 (d, |

TABLE 5-continued

| Compound of formula (I) | yield (% wt) and the $H^1$ NMR ($DMSO-d_6$ or $CDCl_3$): |
|---|---|
| | J = 4.7 Hz, 2H), 3.59 (m, 4H), 3.96 (s, 3H), 6.53 (brs, 2H), 6.54 (s, 1H), 8.07 (s, 1H), 8.17 (s, 1H). MS: (M + 1) = 454.2 |
| 4-amino-5-fluoro-2-methoxy-N-((1-morpholinocycloheptyl)methyl)benzamide (38) | Yellow solid. Yield = 67%. $H^1$ NMR ($DMSO-d_6$): 1.38-1.55 (m, 10H), 1.71-1.79 (m, 2H), 2.56 (m, 4H), 3.33 (s, J = 4.7 Hz, 2H), 3.58 (m, 4H), 3.92 (s, 3H), 6.19 (s, 2H), 6.65 (dd, $J_1$ = 13.6 Hz, $J_2$ = 7.1 Hz, 1H), 7.42 (dd, $J_1$ = 12.1 Hz, $J_2$ = 7.0 Hz, 1H), 7.47 (s, 1H). MS: (M + 1) = 380.2 |
| 4-amino-2,5-difluoro-N-((1-morpholinocycloheptyl)methyl)benzamide (39) | Yellow solid. Yield = 52%. $H^1$ NMR ($DMSO-d_6$): 1.35-1.52 (m, 10H), 1.72-1.78 (m, 2H), 2.53 (m, 4H), 3.30 (s, J = 4.7 Hz, 2H), 3.55 (m, 4H), 6.09 (s, 2H), 6.55 (dd, $J_1$ = 13.6 Hz, $J_2$ = 7.1 Hz, 1H), 7.39 (dd, $J_1$ = 12.1 Hz, $J_2$ = 7.0 Hz, 1H), 7.43 (s, 1H). MS: (M + 1) = 368.3 |
| 6-amino-5-chloro-2-methoxy-N-((1-morpholinocycloheptyl)methyl)nicotinamide (40) | Beige solid. Yield = 70%. $H^1$ NMR ($DMSO-d_6$): 1.21-1.28 (m, 1H), 1.34-1.51 (m, 9H), 1.72-1.78 (m, 2H), 2.53 (m, 4H), 3.31 (d, J = 4.7 Hz, 2H), 3.58-3.60 (m, 4H), 3.98 (s, 3H), 6.95 (s, 2H), 7.98 (s, 1H), 8.07 (t, J = 4.4 Hz, 1H). MS: (M + 1) = 397.2 |
| 6-chloro-N-((1-morpholinocycloheptyl) methyl)imidazo[1,2-a]pyridine-8-carboxamide (41) | Yellow crystalline solid. Yield = 69%. $H^1$ NMR ($DMSO-d_6$): 1.41-1.55 (m, 10H), 1.78-1.84 (m, 2H), 2.58-2.60 (m, 4H), 3.48 (d, J = 5.2 Hz, 2H), 3.63-3.65 (m, 4H), 7.78 (s, 1H), 7.90 (s, 1H), 8.09 (s, 1H), 9.07 (s, 1H), 10.38 (s, 1H). MS: (M + 1) = 392.1 |
| N-((1-morpholinocycloheptyl)methyl) quinoxaline-2-carboxamide (42) | Brown solid. Yield = 50%. $H^1$ NMR ($DMSO-d_6$): 1.42-1.54 (m, 10H), 1.80-1.85 (m, 2H), 2.61-2.63 (m, 4H), 3.42 (d, J = 5.5 Hz, 2H), 3.63-3.65 (m, 4H), 7.98-8.02 (m, 2H), 8.18-8.22 (m, 2H), 8.68 (t, J = 5.3 Hz, 1H), 9.50 (s, 1H). MS: (M + 1) = 369.2 |
| 4-amino-5-chloro-2-methoxy-N-((1-thiomorpholinocycloheptyl)methyl)benzamide (44) | White solid. Yield = 61%. $H^1$ NMR ($CDCl_3$): 1.49-1.61 (m, 10H), 1.79-1.84 (m, 2H), 2.67-2.69 (m, 4H), 2.92-2.93 (m, 4H), 3.49 (d, J = 4.6 Hz, 2H), 4.06 (s, 3H), 7.80 (s, 1H), 8.26 (s, 1H), 8.35 (s, 1H). MS: (M + 1) = 413.3. |
| 4-amino-5-chloro-2-methoxy-N-((1-(4-methylpiperazin-1-yl)cycloheptyl)methyl)benzamide (45) | White solid. Yield = 67%. $H^1$ NMR ($DMSO-d_6$): 1.45-1.56 (m, 12H), 2.50-2.51 (m, 3H), 3.22 (d, J = 5.5 Hz, 2H), 3.33 (m, 8H), 3.83 (s, 3H), 5.95 (s, 2H), 6.49 (s, 1H), 7.72 (s, 1H), 8.02 (s, 1H). MS: (M + 1) = 410.3. |
| 4-amino-5-chloro-N-((1-(4-fluoropiperidin-1-yl)cyclohexyl)methyl)-2-methoxybenzamide (46) | Slightly yellow solid. Yield = 55%. $H^1$ NMR ($DMSO-d_6$): 1.32-1.40 (m, 6H), 1.53-1.60 (m, 2H), 1.63-1.67 (m, 2H), 1.90-2.02 (m, 4H), 2.72-2.85 (m, 4H), 3.40 (d, J = 5.7 Hz, 2H), 3.47 (m, 1H), 3.87 (s, 3H), 5.93 (s, 2H), 6.60 (s, 1H), 7.77 (s, 1H), 7.90 (t, J = 5.8 Hz, 1H). MS: (M + 1) = 399.1. |
| 4-amino-5-chloro-N-((1-(4,4-difluoropiperidin-1-yl)cyclohexyl)methyl)-2-methoxybenzamide (47) | Slightly yellow solid. Yield = 48%. $H^1$ NMR ($DMSO-d_6$): 1.29-1.36 (m, 6H), 1.51-1.54 (m, 2H), 1.64-1.67 (m, 2H), 1.87-1.99 (m, 4H), 2.70 (m, 4H), 3.37 (d, J = 5.5 Hz, 2H), 3.84 (s, 3H), 5.96 (s, 2H), |

TABLE 5-continued

| Compound of formula (I) | yield (% wt) and the $H^1$ NMR ($DMSO-d_6$ or $CDCl_3$): |
| --- | --- |
| | 6.50 (s, 1H), 7.71 (s, 1H), 7.87 (t, J = 5.4 Hz, 1H). MS: (M + 1) = 417.2. |
| 4-amino-5-chloro-N-((1-(4-chlorophenyl)cyclopropyl)methyl)-2-methoxybenzamide (48) | White solid. Yield = 57%. $H^1$ NMR ($CDCl_3$): 0.86-0.89 (m, 2H), 0.96-0.99 (m, 2H), 3.62 (d, J = 5.5 Hz, 2H), 3.72 (s, 3H), 4.37 (brs, 2H), 6.25 (s, 1H), 7.30 (brm, 4H), 7.72 (s, 1H), 8.09 (s, 1H). MS: (M + 1) = 366.0. |
| 4-amino-5-chloro-N-((1-(4-chlorophenyl)cyclobutyl)methyl)-2-methoxybenzamide (49) | White solid. Yield = 53%. $H^1$ NMR ($CDCl_3$): 1.86-1.93 (m, 1H), 2.22-2.33 (m, 5H), 3.65 (s, 3H), 3.83 (d, J = 5.8 Hz, 2H), 6.23 (s, 1H), 7.12 (d, J = 5.8 Hz, 2H), 7.11-7.12 (m, 1H), 7.13-7.14 (m, 1H), 7.32-7.33 (m, 1H), 7.34-7.35 (m, 1H), 7.45 (t, J = 4.8 Hz, 1H), 8.12 (s, 1H). MS: (M + 1) = 380.2. |
| 4-amino-5-chloro-N-((1-(4-chlorophenyl)cyclopentyl)methyl)-2-methoxybenzamide (50) | White solid. Yield = 44%. $H^1$ NMR ($CDCl_3$): 1.73-2.02 (m, 8H), 3.59 (s, 3H), 3.61 (d, J = 5.9 Hz, 2H), 6.21 (s, 1H), 7.29-7.30 (m, 2H), 7.32-7.33 (m, 2H), 7.34-7.35 (m, 1H), 7.40 (t, J = 5.3 Hz, 1H), 8.11 (s, 1H). MS: (M + 1) = 394.1. |
| 4-amino-5-chloro-N-((1-(4-chlorophenyl)cyclohexyl)methyl)-2-methoxybenzamide (51) | White solid. Yield = 84%. $H^1$ NMR ($DMSO-d_6$): 1.42-1.49 (m, 4H), 1.63-1.76 (m, 4H), 2.02-2.06 (m, 2H), 3.57 (s, 3H), 3.62 (d, J = 6.0 Hz, 2H), 6.20 (s, 1H), 7.33-7.39 (m, 6H), 8.11 (s, 1H). MS: (M + 1) = 408.1. |
| 4-amino-5-chloro-N-((1-(4-chlorophenyl)cycloheptyl)methyl)-2-methoxybenzamide (52) | White solid. Yield = 35%. $H^1$ NMR ($CDCl_3$): 1.44-1.53 (m, 4H), 1.55-1.61 (m, 2H), 1.63-1.71 (m, 2H), 1.78-1.84 (m, 2H), 3.52 (s, 3H), 3.61 (d, J = 5.9 Hz, 2H), 6.20 (s, 1H), 7.28-7.38 (m, 7H), 8.09 (s, 1H). MS: (M + 1) = 422.4. |
| 4-amino-5-chloro-N-((1-((4-chlorophenyl)amino)cycloheptyl)methyl)-2-methoxybenzamide (53) | White solid. Yield = 60%. $H^1$ NMR ($dmso-d_6$): 1.36-1.47 (m, 2H, $CH_2$), 1.47-1.66 (m, 8H, $CH_2$), 1.76-1.88 (m, 2H, $CH_2$), 3.49-3.56 (m, 2H, $CH_2$), 3.59 (s, 1H, $CH_3$), 5.36 (bs, 1H, NH), 5.92 (bs, 2H, $NH_2$), 6.42 (s, 1H, Ar), 6.77-6.86 (m, 2H, Ar), 7.05-7.14 (m, 2H, Ar), 7.71 (s, 1H, Ar), 7.85-7.96 (bs, 1H, NH). MS: (M + 1) = 437.2. |
| 4-amino-5-chloro-N-((1-(3,4-dichlorophenyl)cycloheptyl)methyl)-2-methoxybenzamide (54) | Yellowish solid. Yield = 33%. $H^1$ NMR ($CDCl_3$): 1.41-1.47 (m, 2H), 1.55-1.61 (m, 3H), 1.65-1.72 (m, 2H), 1.79-1.85 (m, 2H), 2.07-2.12 (m, 2H), 2.20-2.24 (m, 1H), 3.49 (m, 1H), 3.58 (s, 3H), 3.60 (m, 1H), 4.35 (s, 2H), 6.21 (s, 1H), 7.25 (d, J = 2.3 Hz, 1H), 7.45-7.48 (m, 2H), 8.10 (s, 1H). MS: (M + 1) = 456.1. |
| 4-amino-5-chloro-N-((1-((2-chloro-4-fluorophenyl)amino)cycloheptyl)methyl)-2-methoxybenzamide (E) | White solid. Yield = 67%. $H^1$ NMR ($dmso-d_6$): 1.42-1.60 (m, 8H, $CH_2$), 1.63-1.75 (m, 2H, $CH_2$), 1.78-1.91 (m, 2H, $CH_2$), 3.55-3.61 (m, 2H, $CH_2$), 3.63 (s, 1H, $CH_3$), 4.11-4.30 (bs, 1H, NH), 5.61-6.22 (bs, 2H, $NH_2$), 6.44 (s, 1H, Ar), 6.96-7.10 (m, 2H, Ar), 7.31-7.42 (m, 1H, Ar), 7.71 (s, 1H, Ar), 7.96-7.84 (bs, 1H, NH). MS: (M + 1) = 455.4 |
| 4-amino-5-chloro-2-methoxy-N-((1-((3-(trifluoromethoxy)phenyl)amino)cycloheptyl)methyl)benzamide (F) | Orange solid. Yield = 31%. $H^1$ NMR ($dmso-d_6$): 1.36-1.57 (m, 8H, $CH_2$), 1.58-1.69 (m, 2H, $CH_2$), 1.79-1.92 (m, 2H, $CH_2$), 3.49-3.62 (m, 5H, $CH_3$, $CH_2$), 5.63-5.72 (bs, 1H, NH), 5.87-5.98 (bs, 2H, $NH_2$), |

TABLE 5-continued

| Compound of formula (I) | yield (% wt) and the $H^1$ NMR ($DMSO-d_6$ or $CDCl_3$): |
|---|---|
| | 6.41 (s, 1H, Ar), 6.46-6.53 (m, 1H, Ar), 6.70-6.85 (m, 2H, Ar), 7.10-7.24 (m, 1H, Ar), 7.71 (s, 1H, Ar), 7.83-7.91 (bs, 1H, NH). MS: (M + 1) = 487.0 |
| 6-amino-5-chloro-N-((1-(4-chlorophenyl)cycloheptyl)methyl)-2-methoxynicotinamide (55) | White solid. Yield = 63%. $H^1$ NMR ($DMSO-d_6$): 1.29-1.63 (m, 8H), 1.71 (dd, $J_1$ = 14.2 Hz, $J_2$ = 9.6 Hz, 2H), 2.05 (dd, $J_1$ = 14.4 Hz, $J_2$ = 8.1 Hz, 2H), 3.43 (d, J = 5.8 Hz, 2H), 3.64 (s, 3H), 6.93 (s, 2H), 7.19 (t, J = 5.7 Hz, 1H), 7.40-7.46 (m, 4H), 7.89 (s, 1H). MS: (M + 1) = 423.3. |
| 5-amino-6-chloro-N-((1-(4-chlorophenyl)cycloheptyl)methyl)chroman-8-carboxamide (56) | White solid. Yield = 73%. $H^1$ NMR ($CDCl_3$): 1.42-1.53 (m, 4H), 1.55-1.62 (m, 2H), 1.64-1.72 (m, 2H), 1.78-1.84 (m, 2H), 1.86-1.92 (m, 2H), 2.06-2.15 (m, 2H), 2.68 (t, J = 6.5 Hz, 2H), 3.61 (d, J = 5.9 Hz, 2H), 3.90-3.92 (m, 2H), 7.10 (s, 1H), 7.32-7.38 (m, 5H), 7.49 (t, J = 6.1 Hz, 1H), 8.05 (s, 1H). MS: (M + 1) = 448.2. |
| 4-amino-5-chloro-N-((1-(4-fluorophenyl)cycloheptyl)methyl)-2-methoxybenzamide (57) | White solid. Yield = 46%. %. $H^1$ NMR ($DMSO-d_6$): 0.72-2.06 (m, 12 H), 3.30 (s, 2H), 3.40-3.49 (m, 3H), 5.91 (s, 2H), 6.35 (s, 1H), 7.13-7.25 (m, 2H), 7.36-7.42 (m, 1H), 7.63 (s, 1H) .MS: (M + 1) = 406.2. |
| 4-amino-5-chloro-N-((1-(2-chloro-4-fluorophenyl)cycloheptyl)methyl)-2-methoxybenzamide (58) | White semisolid. Yield = 37%. $H^1$ NMR ($CDCl_3$): 1.44-1.84 (m, 9H), 1.84-2.15 (m, 2H), 2.35 (dd, $J_1$ = 14.8 Hz, $J_2$ = 7.4 Hz, 1H), 3.52 (s, 3H), 3.98 (d, J = 5.9 Hz, 2H), 6.19 (s, 1H), 6.97-7.01 (m, 1H), 7.08 (t, J = 8.7 Hz, 1H), 7.20 (dd, $J_1$ = 8.5 Hz, $J_2$ = 2.8 Hz, 1H), 7.28 (s, 2H), 7.38 (dt, $J_1$ = 13.0 Hz, $J_2$ = 6.5 Hz, 1H), 8.10 (s, 1H). MS: (M + 1) = 440.1. |
| 4-amino-5-chloro-2-methoxy-N-((1-(4-(trifluoromethyl)phenyl)cycloheptyl)methyl)benzamide (59) | White solid. Yield = 47%. MS: (M + 1) = 456.2. |
| 4-amino-5-chloro-2-methoxy-N-((1-(5-(trifluoromethyl)pyridin-2-yl)cycloheptyl)methyl)benzamide (60) | White solid. Yield = 52%. MS: (M + 1) = 457.3. |
| 4-amino-5-chloro-2-methoxy-N-((1-(pyridin-3-yl)cycloheptyl)methyl)benzamide (61) | Slight green solid. Yield = 41%. MS: (M + 1) = 489.2. |

Starting from the compound 36, it was further synthesized the 4-amino-5-chloro-2-hydroxy-N-((1-morpholinocycloheptyl)methyl)benzamide (43):

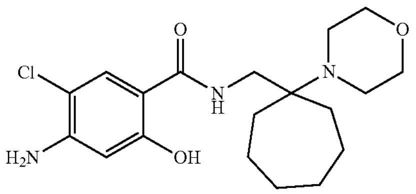 [SMILES: Nc1cc(O)c(C(=O)NCC2(N3CCOCC3)CCCCCC2)cc1Cl]

as follows: to a solution of 4-amino-5-chloro-2-methoxy-N-((1-morpholinocycloheptyl) methyl) benzamide (compound 36, 0.183 mmol, 0.080 g) in dry $CH_2Cl_2$ (1 mL), a 1M solution of $BBr_3$ in $CH_2Cl_2$ (0.201 mL, 0.201 mmol) was added at 0° C. under Ar. The mixture was then stirred at the same temperature for 1.5 h. The reaction mixture was quenched with sat. $NH_4Cl$ (10 mL), extracted with EtOAc (3×10 mL), the combine organic phase was washed with brine (10 mL), dried and concentrated in vacuum. The residue was purified by column chromatography eluted with EtOAc:hexane 4:1. Beige crystalline solid. Yield=48%. $H^1$ NMR ($DMSO-d_6$): 1.41-1.57 (m, 10H), 1.74-1.80 (m, 2H), 2.51-2.54 (m, 4H), 3.33 (m, 2H), 3.58 (m, 4H), 5.98 (s, 2H), 6.53 (s, 1H), 7.75 (s, 1H), 8.13 (s, 1H). MS: (M+1)=383.2, (M−1)=380.8.

Pharmacological Tests

1. Materials and Methods

I. In Vitro Tests

The effect of the test compounds was first evaluated in vitro either on activated peritoneal macrophages or on activated primary SFs. For the purposes of these in vitro assays the test compounds were reconstituted in DMSO to a concentration of 100 mM and all further dilutions were performed using 1×DMEM (Gibco, 41966-029) supplemented with 0.5% FBS and 50 U/ml Penicillin Streptomycin (P/S).

A) Anti-Inflammatory Potential Assessed on Activated Peritoneal Macrophages.

Activated peritoneal macrophages were isolated from the peritoneal lavage of C57BL/6 wild type mice, 5 days after the peritoneal administration of 3% Thioglucolate, as described in Jiménez-García et al., 2015. The isolated cells were seeded at a concentration of $5\times10^5$ cells/well in a 48 well plate. 4 h after isolation, cells were starved O/N in Optimem (Gibco, 11058, 100 U/ml P/S). The cells were further activated with 100 ng/ml Lipopolysaccharide (LPS, Sigma-Aldrich, L2630) along with the test compounds at a dose of 10 μM. 48 h later the supernatants of the cell cultures were collected and analyzed using the Mouse 13 plex Legendplex Chemokine (Biolegend, 740007) and Cytokine (Bioloegend, 740446) panels according the manufacturer's instructions.

The same protocol was repeated reducing the concentration of LPS to 10 ng/ml in order to determine the efficiency of the tested compounds.

B) Anti-Inflammatory Potential Assessed on Activated SFs

Primary SFs were derived from a) human TNF transgenic (hTNFTg) mice (Keffer et al., 1991) as well as from b) CBA/C57BL6 wild type mice.

hTNFtg mice overexpress human TNF, resulting in the spontaneous development of arthritis. The SFs derived from these mice exhibit an activated phenotype that includes the secretion of human TNF as well as of other inflammatory cytokines such as IL-6, MCP-1 and chemokines such as CCL5 and CCL20.

Wild type derived SFs do not normally exhibit an activated phenotype and therefore, for the purposes of this screening, they were activated following treatment with 10 ng/ml hTNF (Peprotech, 300-01A). By testing the compounds in a) and b) we accessed their effect on the activated SFs phenotype caused by both the endogenous hTNF upregulation and the exogenous hTNF administration. In this way it was confirm the ability of the compounds of the invention to act in the TNF pathway directly downstream of TNF.

SFs were isolated as previously described by Armaka et al., 2009, from the ankle joints of hTNFtg or CBA/C57BL6 wild type (wt) littermates. Briefly, ankle joints were digested with Collagenase IV (Sigma Aldrich, C5138) for 45 minutes at a 37° C. shaking waterbath and after 5 days in culture at 37° C. and 5% $CO_2$, a depletion of CD45+ lineage cells was performed using a Biotin anti-mouse CD45 Antibody (Biolegend, 103104) and Dynabeads™ Biotin Binder (ThermoFisher 11047), according to the manufacturer's protocol. After 10 days in culture, SFs were seeded overnight (O/N) at a concentration of $2\times10^4$ cells/well in a 96 well plate in 1×DMEM, supplemented with 100 U/ml Penicillin Streptomycin (P/S) and 10% Fetal Bovine Serum (FBS). The next day the cells were synchronized by starvation that included their O/N plating in low serum medium (0.5% FBS). Following the O/N starvation, the hTNFg and the WT SFs were treated with different concentrations of the experimental compounds. The SFs were at the same time activated with 10 ng/ml hTNF (Peprotech, 300-01A). 48 h following the treatment the cell culture supernatants were collected and analyzed by ELISA (R&S Systems, Duoset, DY478 and DY760) according to the manufacturer's protocol, for the detection of CCL5/Rantes and CCL20/Mip3, two known inflammatory chemokines. The IC50 values were determined as the concentration of the compounds required to reduce the levels of secreted CCL5 and CCL20 by 50%.

The supernatants of the SFs were also analyzed using the Mouse pro-inflammatory chemokine panel from Legendplex™ (Biolegend, 740007), according to manufacturer's instructions, for the simultaneous detection of 13 Mouse chemokines.

In order to determine the efficiency of the compounds of the invention, the same protocol was repeated with some minor modifications. Mainly, the concentration of hTNF was 10-fold reduced, i.e., adjusted to 1 ng/ml, and the SFs were seeded overnight at a concentration of $10^4$ cells/well.

C) Determination of Compound Cytotoxicity

The toxicity of the test compounds was assessed at several concentrations using the Crystal Violet assay on both SFs and PMCs. Adherent viable cells were Methanol fixed and stained with Crystal Violet. Optical density was quantified at 570 nM, as described in Feoktistova et al., 2016.

D) Wound Healing Assay

Activated SFs were isolated from hTNFtg mice as described above and they were seeded in 24 well plates at a concentration of $2\times10^5$ cells/well. The next day a straight-line wound was created on the formed cell monolayer using the tip of a 200 μl pipette. Images of the wounds were captured by microscope at a magnification of 4× at two time points. Time point 0 (i.e. the time of the creation of the wound) as well as 24 h later (t=24 h). The area of the wound was measured at each time point using the software ImageJ.

The percent closure of the wound was calculated using the following formula:

$$[(\text{wound area at } t0 - \text{wound area at } t24)/\text{wound area at } t0]*100$$

The assay for each compound was repeated four times.

II) In Vivo Tests

In order to evaluate in vivo the anti-inflammatory effect of the test compounds a model of in vivo LPS acute systemic inflammation was used where C57BL/6J mice were challenged by administration of 1 μg LPS. Each one of the compounds 51 to 53 was administered to C57BL/6J mice per os in two doses of 50 mg. Two hours after administering the first dose, the animals received the second p.o. dose of each compound and were also challenged with 1 μg LPS intraperitoneally. Sera samples were collected 1.5 hrs post induction in order to measure the levels of 13 cytokines using the pro-inflammatory panel from Legendplex (cat no 740446) and following manufacturer's instructions. Four biological replicates were performed and the average and SEM were calculated with the obtained results.

The same protocol was followed but administering compound 53 at 100 mg/kg. In this case both the levels of the 13 cytokines but also of 13 chemokines were measured, using the pro-inflammatory panel from Legendplex (cat no 740007).

2. Results

I) In Vitro Results

A) the Test Compounds Exhibit Anti-Inflammatory Activity on Thioglycolate Activated Peritoneal Macrophages.

In order to assess the anti-inflammatory activity of the compounds of the invention, their ability to reduce the levels of secreted cytokines and chemokines from activated macrophages, which are key inflammatory cells of the immune system, was measured. Test compounds 51, 52 and 53, E and F were tested at a dose of 10 μM on LPS induced thioglycolate derived peritoneal macrophages. Chemokine and cytokine analyses were performed using the Mouse pro-inflammatory panels from Legendplex and their levels are presented as a percentage of the levels detected in the untreated control cells (Tables 6a and 6b). Data presented for compounds 51, 52, 53 refer to LPS stimulation of 100 ng/ml, while compounds E and F were tested upon LPS stimulation of 10 ng/ml.

The data above show that the tested compounds can effectively ameliorate inflammatory cytokines and chemokines secreted from activated macrophages thus supporting that they may play an anti-inflammatory role in the context of inflammatory conditions.

TABLE 6a

| | LPS activated thioglyclolate peritoneal macrophages | | | | | |
|---|---|---|---|---|---|---|
| Chemokines | untreated | 51 | 52 | 53 | E | F |
| MCP1 | 100 | 27 | 28 | 75 | 9.3 | 9 |
| MIP1α | 100 | | | 60 | 50 | 45 |
| MIP1β | 100 | 90 | 51 | 67 | 41 | 26 |
| CCL5 | 100 | | | 22 | 8 | 2 |
| MDC | 100 | | | 52 | 54 | 47 |

| | LPS activated thioglyclolate peritoneal macrophages | | | | | |
|---|---|---|---|---|---|---|
| Cytokines | untreated | 51 | 52 | 53 | E | F |
| IL1α | 100 | 36 | 9 | 30 | | |
| IL12p70 | 100 | 54 | 23 | 18 | | |
| IL6 | 100 | 44 | 7 | 15 | 8.8 ($IC_{50}$ = 0.57) | 5.3 ($IC_{50}$ = 2.67) |
| IL27 | 100 | 77 | 19 | 75 | | |
| GMCSF | 100 | 80 | 36 | 38 | | |

B) The Test Compounds Exhibit Anti-Inflammatory Potential on Activated SFs

The in vitro effect of the tested compounds was also evaluated on activated synovial fibroblasts to examine the possibility that these test compounds could directly affect a cell type that plays an instrumental role in rheumatoid arthritis and thus support their possible therapeutic effect on arthritis.

When the test compounds were applied on activated SFs they were shown to downregulate the levels of two pro-inflammatory chemokines CCL5 and CCL20, which were elevated in both hTNFtg and hTNF-activated wt SFs. The results of this analysis together with their cytotoxicity data are presented in Tables 7 and 8 below.

Table 7 summarizes the reduction of CCL5 and CCL20 levels achieved with the test compounds of the invention. Data are presented as percentages of the chemokine levels detected in treated cells compared to 100% levels of the chemokines detected in the untreated cells.

TABLE 7

| | | CCL5 | | CCL20 | |
|---|---|---|---|---|---|
| Test Compounds | CONCENTRATION | WT (10 ng/mL/ 1 ng/mL hTNF) | hTNFtg | WT (10 ng/mL/ 1 ng/mL hTNF) | hTNFtg |
| Untreated hTNFTg SF | — | NA | 100 | NA | 100 |
| hTNF induced wt SF (10 or 1 ng/mL) | — | 100/100 | NA | 100/100 | NA |
| 44 | 10 μM | 30/ND | 69 | 75/ND | 45 |
| | 50 μM | 2/ND | 26 | 46/ND | 27 |
| 51 | 10 μM | 67/54 | 46 | 14/63 | 16 |
| | 50 μM | 39/20 | 47 | 5/35 | 13 |
| 52 | 10 μM | 27/48 | 50 | 15/45 | 67 |
| | 50 μM | 14/22 | 29 | **/17 | 48 |
| 53 | 10 μM | 35/16 | 40 | 15/26 | 22 |
| | 50 μM | 26/8 | 34 | 8/9 | 22 |
| 55 | 10 μM | 89/ND | 49 | 79/ND | 78 |
| | 50 μM | 26/ND | 13 | 24/ND | 57 |
| 57 | 10 μM | 49/MD | 40 | 13/ND | 27 |
| | 25 μM | 14/ND | 40 | 6/ND | 25 |
| 58 | 10 μM | 0/8 | 64 | 48.5/15 | 32.5 |
| | 25 μM | 0/9 | 53.5 | 0/14 | 22.5 |
| E | 10 μM | 13/0 | 8.2 | 5/2 | 14 |
| | 25 μM | 11/0 | 5 | 2/3 | 20 |
| F | 10 μM | 12/0 | 0 | 11/11 | 24 |
| | 25 μM | 9/0 | 0 | 10/7 | 29 |

ND: not determined.

Table 8 summarizes the values of IC50 and toxicity for the test compounds of the invention. Dose response curves regarding the WT SFs were produced with 10 ng/ml hTNF stimulation for all compounds, with the exception of the compounds E and F, where WT cells were induced using hTNF at 1 ng/ml:

TABLE 8

| | IC50 (μM) CCL5 | | IC50 (μM) CCL20 | | Cell Toxicity |
|---|---|---|---|---|---|
| Compound | WT | hTNFtg | WT | hTNFtg | (μM) |
| 44 | 3.7 | 12.6 | ≈65 | ≈15 | >100 |
| 51 | 10.4 | 2.6 | 3.0 | 1.0 | >100 |
| 52 | 1.4 | 4.2 | 1.5 | 15 | >200 |
| 53 | 2.9 | 2.3 | 2.3 | 3.2 | >100 |
| 55 | 35 | 16 | 25 | >25 | >50 |

TABLE 8-continued

| | IC50 (μM) CCL5 | | IC50 (μM) CCL20 | | Cell Toxicity |
|---|---|---|---|---|---|
| Compound | WT | hTNFtg | WT | hTNFtg | (μM) |
| 57 | 18 | 4 | 3.5 | 2.4 | >25 |
| 58 | 2.96 | 0.95 | 2.44 | 0.74 | >50 |
| E | 0.59 | 1.69 | 0.167 | 4.07 | >150 |
| F | 0.090 | <0.010 | 0.129 | <0.010 | >25 |

The anti-inflammatory potential of the test compounds 51, 52, 53, E and F on SFs was also assessed using the Mouse pro-inflammatory chemokine panel from Legendplex that allows the simultaneous detection of 13 Mouse chemokines. The effect of compound 51 on SFs was assessed at a dose of 25 μM, while the effect of the test compounds 52, 53, E and F was assessed at a dose of 10 μM. The test compounds ameliorated the levels of the secreted chemokines EOTAXIN, KC, LIX, MCP1 and MIP1β as shown in Table 8. Numbers represent percentages of the chemokine levels secreted from the treated SFs compared to 100% levels of the chemokines detected in the untreated cells (i.e. either hTNFTg SFs or hTNF-activated wt SFs).

Table 9 summarizes the effect of the test compounds 51, 52 and 53, E and F on the inflammatory chemokines secreted from activated SFs. WT SFs were stimulated with 10 ng/ml hTNF.

TABLE 9

| | hTNFTg | | | | | | WT | | | |
|---|---|---|---|---|---|---|---|---|---|---|
| Chemokine | untreated | 51 | 52 | 53 | E | F | untreated | 51 | 52 | 53 |
| EOTAXIN | 100 | 24 | 6 | 9 | 2.5 | 0 | 100 | 7 | 26 | 59 |
| KC | 100 | 80 | 49 | 49 | 32 | 35 | 100 | 41 | 34 | 68 |
| LIX | 100 | 22 | 48 | 40 | 19.5 | 1 | 100 | 3 | 23 | 24 |
| MCP1 | 100 | 89 | 55 | 49.5 | 25.5 | 13.5 | 100 | 59 | 40 | 57 |
| MIP1β | 100 | | | 33 | 24 | 12.5 | | | | |

The data presented above support that the compounds of the invention can downregulate the levels of inflammatory chemokines from activated SFs, while exhibiting low cytotoxicity, thus supporting that these compounds may be efficient in affecting the arthritogenic phenotype of activated SFs and consequently may have a therapeutic effect on arthritis.

As the synovial fibroblasts have been demonstrated to be the cellular drivers of arthritic pathologies, the effect of the test compounds on activated SFs provides supporting evidence that these test compounds could be used as an alternative effective small molecule treatment for the therapy of arthritis.

As the SFs have been demonstrated to be the cellular drivers of arthritic pathologies, the effect of the test compounds on activated SFs provides supporting evidence that these test compounds could be used as an alternative effective small molecule treatment for the therapy of arthritis.

C) The Test Compounds Reduce the Migration and Proliferation Potential of Activated SFs Another feature of the activated phenotype of the arthritogenic SFs is their ability to exhibit increased proliferation and migration properties. The inventors wanted to further explore the potential of the test compounds to reduce the activated phenotype of the arthritogenic SFs and studied their effect on a wound healing assay. In this assay a wound is formed on a monolayer of SFs and the rate of closure of this wound is indicative of the proliferation and migration capacity of the SFs, i.e. the slower the closure of the wound, the less proliferative and migratory are the SFs.

The potential ability of the compounds 53, E and F to inhibit the proliferation and migration of activated SFs, was assessed at a concentration of 10 μM and the wound healing assay was performed using hTNFtg SFs, as these cells show increased proliferation and migration potential (Vasilopoulos et al., 2007). The data shown in Table 10 where the percentages of wound closure area are presented in hTNFtg untreated as well as compound treated cells.

TABLE 10

| | hTNFtg | | | |
|---|---|---|---|---|
| Treatment | untreated | 53 | E | F |
| % of wound closure (mean ± SD) | 100 ± 19.9 | 67.7 ± 16.2 | 73 ± 31.5 | 63 ± 11.8 |

The results of this analysis show that the different test compounds may remarkably affect the proliferative and migratory capacity of activated SFs and may thus have a therapeutic effect in diseases where fibroblasts play a major pathogenic role as is the case of arthritis.

II) In Vivo Results

The anti-inflammatory effect of the test compounds 51, 52 and 53 was assessed in vivo in the LPS model of acute inflammation. Administration of the endotoxin Lipopolysaccharide (LPS) to mice induces acute inflammatory responses similar to the inflammatory response that occurs during the early stages of septic shock. Shortly after administration of the endotoxin, cytokines and chemokines are released. This model is fast, cost-effective and widely used for screening of anti-inflammatory properties of test items aimed for treatment of a number of inflammatory and autoimmune conditions (Seemann et al., 2017; Stortz et al., 2017).

Sera samples from the treated mice with the 50 mg/Kg doses of the test compounds 51-53 were evaluated using the mouse pro-inflammatory panel of Legendplex and the data acquired are presented as pg/ml in Table 11. Vehicle, 52 and 53 were tested in quadruplicates (vehicle_1-4), 51 in triplicate (51_1-3). Table 11 summarizes results from one experiment out of a triplicate of experiments.

TABLE 11

| | | IL-1α | MCP-1 | IL-1β | IL-10 | IL-6 | IL-17A |
|---|---|---|---|---|---|---|---|
| Treatment | Average | 82.4 | 13376.8 | 138.0 | 782.5 | 6763.1 | 125.3 |
| Vehicle | SEM | 16.4 | 6032.3 | 32.5 | 89.8 | 317.4 | 20.8 |
| 51 | Average | 27.4 | 4689.1 | 87.0 | 1774.5 | 4702.5 | 43.8 |
| | SEM | 8.5 | 855.8 | 5.5 | 203.0 | 1074.4 | 8.8 |
| 52 | Average | 43.1 | 4916.5 | 118.5 | 1692.2 | 3988.8 | 27.7 |
| | SEM | 21.0 | 541.0 | 29.1 | 702.3 | 630.8 | 6 |
| 53 | Average | 67.3 | 5149 | 113.1 | 2616.1 | 5145 | 55.1 |
| | SEM | 35.2 | 1242.8 | 24.5 | 837.1 | 753.4 | 18.9 |

Sera samples from the treated mice with test compounds 53 with 100 mg/Kg were also evaluated using the mouse pro-inflammatory cytokine and chemokine panel of Legendplex and the effect of compound 53 at a higher dose (100 mg/kg) in inhibiting inflammatory cytokines and chemokines is presented in the Table 12 below.

TABLE 12

| Cytokine | | vehicle | 53 p.o. | p-value |
|---|---|---|---|---|
| IL-23 | Average | 43.1 | 16.6 | 0.0286 |
| | SEM | 2.5 | 3.4 | |
| TNF- α | Average | 831.1 | 136.8 | 0.0286 |
| | SEM | 180.1 | 31.0 | |
| IFN-γ | Average | 15.1 | 6.7 | 0.0286 |
| | SEM | 2.1 | 0.9 | |
| IL12p70 | Average | 11.2 | 5.7 | 0.0286 |
| | SEM | 0.9 | 0.8 | |
| IL-1β | Average | 24.3 | 12.4 | 0.0286 |
| | SEM | 2.0 | 1.7 | |
| IL-27 | Average | 26.7 | 16.1 | 0.0286 |
| | SEM | 3.5 | 2.5 | |
| IL-17A | Average | 7.1 | 3.7 | 0.0286 |
| | SEM | 0.6 | 0.6 | |
| GM-CSF | Average | 16.4 | 9.8 | 0.0286 |
| | SEM | 1.3 | 1.3 | |
| KC | Average | 7273.8 | 4227.5 | 0.0286 |
| | SEM | 201.2 | 886.0 | |
| MCP1 | Average | 2858.5 | 1246.2 | 0.0286 |
| | SEM | 201.9 | 344.3 | |
| IP-10 | Average | 146.4 | 45.2 | 0.0286 |
| | SEM | 42.3 | 2.6 | |
| MIP-1A | Average | 790.5 | 244.3 | 0.0286 |
| | SEM | 135.2 | 56.1 | |
| MIP-1B | Average | 3198.7 | 1301.1 | 0.0286 |
| | SEM | 293.3 | 352.2 | |
| MDC | Average | 99.6 | 56.6 | 0.048 |
| | SEM | 16.2 | 6.5 | |

The data above show that the compounds of the invention can effectively reduce the levels of several inflammatory cytokines, namely IL1α, IL6, IL17A, IL1β, IL-23, TNF-α, IFN-γ, IL12p70, IL-1β, IL-27, IL-17A, GM-CSF, and KC while they increased the levels of the cytokine IL10 which is known to have potent anti-inflammatory activities.

Not only that, but also, the compounds of the invention were also able to reduce the levels of chemokines MCP-1, MIP-1Am MIP-1B, IP-10 and MDC (see Table 12).

Overall, the data above complement the in vitro data and support that the compounds provided in this invention exhibit also in vivo an anti-inflammatory potential and could therefore have a therapeutic effect in treating inflammatory conditions.

CITATION LIST

Patent Literature

WO2006/112828 A1; and

US2013/0096319A1.

Non Patent Literature

Armaka, M. et al., "A standardized protocol for the isolation and culture of normal and arthritogenic murine synovial fibroblasts". Protoc. Exch. 2-5 (2009). doi:10.1038/nprot.2009.102;

Becker D. P. et al., "Pyrrolizidine esters and anides as 5-HT4 receptor agonists and antagonists", J. Med. Chem., 2006, 49, 1125-1139;

Estrada A. A. et al., "Discovery of Highly Potent, Selective, and Brain-Penetrable Leucine-Rich Repeat Kinase 2 (LRRK2) Small Molecule Inhibitors", J. Med. Chem., 2012, 55, 9416-9433;

Albericio F. et al., "Choosing the Right Coupling Reagent for Peptides. A Twenty-Five-Year Journey", Org. Process Res. Dev., 2018, 22, 760-772;

Feoktistova et al., "Crystal Violet Assay for Determining Viability of Cultured Cells", Cold Spring Harb Protoc, 2016; doi:10.1101/pdb.prot087379;

Jiménez-García, L., et al., "Thioglycollate-elicited Peritoneal Macrophages Preparation and Arginase Activity Measurement in IL-4 Stimulated Macrophages", Bio-protocol 5(17): e1585. DOI: 10.21769/BioProtoc.1585;

Keffer et al., "Transgenic mice expressing human tumour necrosis factor: a predictive genetic model of arthritis", EMBO Journal, 1991, 10(13), 4025-4031, 1991;

Matikonda S. S. et al., "Mechanistic Evaluation of Bioorthogonal Decaging with trans-Cyclooctene: The Effect of Fluorine Substituents on Aryl Azide Reactivity and Decaging from the 1,2,3-Triazoline", Bioconj. Chem., 2018, 29, 324-334;

Rassias G. et al., "Investigation of Synthetic Routes to a Key Benzopyran Intermediate of a 5HT4", Organic Process Research & Development 2010, 14, 92-98.

Seemann, S., et al., "Comprehensive comparison of three different animal models for systemic inflammation", J Biomed Sci, 2017, 24: 60. doi.org/10.1186/s12929-017-0370-8; and Stortz, J. A., et al., "Murine Models of Sepsis and Trauma: Can We Bridge the Gap?", ILAR J., 2017, 58(1), 90-105.

Vasilopoulos et al., "Actin cytoskeleton dynamics linked to synovial fibroblast activation as a novel pathogenic principle in TNF-driven arthritis", Ann Rheum Dis, 2007; 66(Suppl III):iii23-iii28.

CLAUSES

For reasons of completeness, various aspects of the invention are set out in the following numbered clauses:

Clause 1. A compound of formula (I):

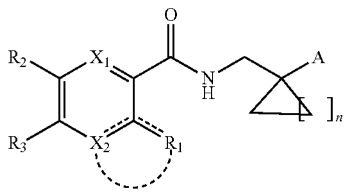

(I)

or a pharmaceutically acceptable salt, hydrate, or isomer thereof, wherein:

$R_1$ represents halogen; —$OR_4$; ($C_1$-$C_{10}$)alkyl; or ($C_1$-$C_{10}$) alkyl substituted with one or more substituents, the same or different, selected from OH, halogen, ($C_1$-$C_6$) alkyl, —O—($C_1$-$C_6$)alkyl, nitro, cyano, and halogen; or, alternatively, $R_1$ together with $X_2$ forms an aromatic, saturated or partially saturated known ring, the ring having 5 or 6 members selected from the group consisting of: —$C(R_x)_2$—, —$CR_x$—, —N—, —$NR_x$—, S, and O;

- - - represents a single bond or a double bond:

$R_2$ represents —OH; halogen; ($C_1$-$C_{10}$)alkyl; ($C_1$-$C_{10}$) alkyl substituted with one or more substituents, the same or different, selected from OH, halogen, ($C_1$-$C_6$) alkyl, —O—($C_1$-$C_6$)alkyl, nitro, cyano, and halogen; —$S(O)_2R_4$; an aromatic known ring system comprising 5 or 6 members selected from —$CR_a$—, and —N—;

$R_3$ represents —$NR_5R_6$, being $R_5$ and $R_6$ the same or different and being selected from —H, ($C_1$-$C_{10}$)alkyl, ($C_3$-$C_{10}$)cycloalkyl, and an aromatic known ring system comprising 5 or 6 members selected from —$CR_b$—, and —N—; or, alternatively, $R_2$ together with $R_3$ form an aromatic, saturated or partially saturated known ring, the ring having 5 or 6 members selected from —$C(R_y)_2$—, —$CR_y$—, —N—, —$NR_y$, —S—, and —O—;

A is a known ring system having from 1 to 3 rings and comprising from 4 to 14 members, each one of the members being selected from, —$C(R_z)_2$—, —$CR_z$—, —N—, —$NR'_z$—, —S—, —Se—, —$SO_2$, —$SeO_2$, and —O—; the rings being saturated, partially unsaturated, or aromatic; and being fused or isolated;

n represents a enter value comprised from 1 to 7;

$X_1$ and $X_2$ are the same or different and represent C or N atom;

$R_4$ represents —H; ($C_1$-$C_{10}$) alkyl; or ($C_1$-$C_{10}$) alkyl substituted with one or more substituents, the same or different, selected from OH, halogen, ($C_1$-$C_6$)alkyl, —O—($C_1$-$C_6$)alkyl, nitro, cyano, and halogen;

the term "($C_3$-$C_{10}$)cycloalkyl" refers to a saturated carbocyclic ring containing from 3 to 10 carbon atoms;

each one of $R_a$ is independently selected from the group consisting of —H, —OH, halogen, ($C_1$-$C_6$)alkyl, and ($C_1$-$C_6$)alkyl substituted with one or more substituents, the same or different, selected from: OH, halogen, ($C_1$-$C_6$)alkyl, —O—($C_1$-$C_6$)alkyl, nitro, cyano, and halogen;

each one of $R_b$ is independently selected from the group consisting of —H, —OH, halogen, ($C_1$-$C_6$)alkyl, and ($C_1$-$C_6$)alkyl substituted with one or more substituents, the same or different, selected from: OH, halogen, ($C_1$-$C_6$)alkyl, —O—($C_1$-$C_6$)alkyl, nitro, cyano, and halogen;

$R_t$ represents ($C_1$-$C_{10}$) alkyl;

each one of the $R_x$ is independently selected from the group consisting of —H, —OH, ($C_1$-$C_6$)alkyl, ($C_1$-$C_6$) haloalkyl, —O—($C_1$-$C_6$)alkyl, nitro, —$NR_7$—, —$NR_8R_9$, and halogen;

each one of the $R_y$ is independently selected from the group consisting of —H, —OH, ($C_1$-$C_6$)alkyl, ($C_1$-$C_6$) haloalkyl, —O—($C_1$-$C_6$)alkyl, nitro, —$NR_{10}$—, —$NR_{11}R_{12}$, and halogen;

each one of the $R_z$ and R'z is independently selected from the group consisting of —H, —OH, ($C_1$-$C_6$)alkyl, ($C_1$-$C_6$)haloalkyl, —O—($C_1$-$C_6$)alkyl, nitro, —$NR_{13}$—, —$NR_{12}R_{15}$, and halogen;

and each one of $R_7$ to $R_{15}$ is independently selected from the group consisting of H, ($C_1$-$C_6$)alkyl, ($C_1$-$C_6$)haloalkyl, and —O—($C_1$-$C_6$)alkyl.

Clause 2. The compound of clause 1, wherein R'z is selected from ($C_1$-$C_6$)alkyl, and ($C_1$-$C_6$)haloalkyl Clause 3. The compound of any one of the clauses 1-2, which is one of formula (Ia):

(Ia)

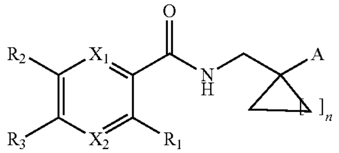

wherein $R_1$, $R_2$, $R_3$, $X_1$, $X_2$, A and n are as defined above.

Clause 4. The compound of any one of the preceding clauses, wherein $R_1$ is selected from —OH, —O—($C_1$-$C_{10}$)alkyl, and halogen; or alternatively, $R_1$ together with $X_2$ forms a partially saturated or aromatic known ring having 5 or 6 members, the members being as defined above.

Clause 5. The compound of any one of the preceding clauses, wherein $R_2$ represents halogen or —$S(O)_2R_t$.

Clause 6. The compound of any one of the preceding clauses, wherein $R_3$ represents —$NR_6R_7$, being $R_6$ and $R_7$ the same, particularly being H: or, alternatively $R_3$ together with $R_2$ form an aromatic or partially saturated known ring, the ring having 5 or 6 members as defined above.

Clause 7. The compound of any one of the preceding clauses, wherein A is selected from:

an aryl ring comprising 5 or 6 members as defined in clause 1, and a saturated ring comprising from 4 to 8 members, particularly a ring having 5 or 6 members, as defined in clause 1.

Clause 8. The compound of clause 6, wherein A is a known 6-membered ring selected from:

a known aryl wherein one of the members is —N—, and the other members forming the 6-membered ring are —$CR_z$—, each one of the $R_z$ being independently selected from: H, ($C_1$-$C_6$)haloalkyl, and halogen;

a known aryl ring having 6 —$CR_z$— members, each one of the $R_z$ being independently selected from: H, ($C_1$-$C_6$)haloalkyl, —$NR_7$—, and halogen; and a saturated known ring, wherein one or two of the members are selected from —$NR_z$—, —S—, and —O— and the other members forming part of the ring represent —$C(R_z)_2$—, each one of the $R_z$ being independently selected from: H, ($C_1$-$C_6$)alkyl, and halogen.

Clause 9. The compound of any one of the preceding clauses, which is selected from the group consisting of:

4-amino-5-chloro-2-methoxy-N-((1-morpholinocycloheptyl)methyl)benzamide;

4-amino-5-(ethylsulfonyl)-2-methoxy-N-((1-morpholinocycloheptyl)methyl)benzamide;

4-amino-5-fluoro-2-methoxy-N-((1-morpholinocycloheptyl)methyl)benzamide;

4-amino-2,5-difluoro-N-((1-morpholinocycloheptyl)methyl)benzamide;

6-amino-5-chloro-2-methoxy-N-((1-morpholinocycloheptyl)methyl)nicotinamide;

6-chloro-N-((1-morpholinocycloheptyl)methyl)imidazo[1,2-a]pyridine-8-carboxamide;

N-((1-morpholinocycloheptyl)methyl)quinoxaline-2-carboxamide;

4-amino-5-chloro-2-hydroxy-N-((1-morpholinocycloheptyl)methyl)benzamide;

4-amino-5-chloro-2-methoxy-N-((1-thiomorpholinocycloheptyl)methyl)benzamide;

4-amino-5-chloro-2-methoxy-N-((1-(4-methylpiperazin-1-yl)cycloheptyl)methyl)benzamide;

4-amino-5-chloro-N-((1-(4-fluoropiperidin-1-yl)cyclohexyl)methyl)-2-methoxybenzamide;

4-amino-5-chloro-N-((1-(4,4-difluoropiperidin-1-yl)cyclohexyl)methyl)-2-methoxybenzamide;

4-amino-5-chloro-N-((1-(4-chlorophenyl)cyclopropyl)methyl)-2-methoxybenzamide;

4-amino-5-chloro-N-((1-(4-chlorophenyl)cyclobutyl)methyl)-2-methoxybenzamide;

4-amino-5-chloro-N-((1-(4-chlorophenyl)cyclopentyl)methyl)-2-methoxybenzamide;

4-amino-5-chloro-N-((1-(4-chlorophenyl)cyclohexyl)methyl)-2-methoxybenzamide;

4-amino-5-chloro-N-((1-(4-chlorophenyl)cycloheptyl) methyl)-2-methoxybenzamide;
4-amino-5-chloro-N-((1-((4-chlorophenyl)amino)cycloheptyl)methyl)-2-methoxybenzamide;
4-amino-5-chloro-N-((1-(3,4-dichlorophenyl)cycloheptyl) methyl)-2-methoxybenzamide;
6-amino-5-chloro-N-((1-(4-chlorophenyl)cycloheptyl) methyl)-2-methoxynicotinamide;
5-amino-6-chloro-N-((1-(4-chlorophenyl)cycloheptyl) methyl)chroman-8-carboxamide;
4-amino-5-chloro-N-((1-(4-fluorophenyl)cycloheptyl) methyl)-2-methoxybenzamide;
4-amino-5-chloro-N-((1-(2-chloro-4-fluorophenyl)cycloheptyl)methyl)-2-methoxybenzamide;
4-amino-5-chloro-2-methoxy-N-((1-(4-(trifluoromethyl) phenyl)cycloheptyl)methyl) benzamide;
4-amino-5-chloro-2-methoxy-N-((1-(5-(trifluoromethyl) pyridin-2-yl)cycloheptyl)methyl) benzamide; and
4-amino-5-chloro-2-methoxy-N-((1-(pyridin-3-yl)cycloheptyl)methyl)benzamide.

Clause 10. The compound of formula (I) according to clause 9, which is selected from:
4-amino-5-chloro-2-methoxy-N-((1-thiomorpholinocycloheptyl)methyl)benzamide;
4-amino-5-chloro-N-((1-(4-chlorophenyl)cyclohexyl) methyl)-2-methoxybenzamide;
4-amino-5-chloro-N-((1-(4-chlorophenyl)cycloheptyl) methyl)-2-methoxybenzamide;
4-amino-5-chloro-N-((1-((4-chlorophenyl)amino)cycloheptyl)methyl)-2-methoxybenzamide;
4-amino-5-chloro-N-((1-(3,4-dichlorophenyl)cycloheptyl) methyl)-2-methoxybenzamide;
6-amino-5-chloro-N-((1-(4-chlorophenyl)cycloheptyl) methyl)-2-methoxynicotinamide;
4-amino-5-chloro-N-((1-(4-fluorophenyl)cycloheptyl) methyl)-2-methoxybenzamide; and
4-amino-5-chloro-N-((1-(2-chloro-4-fluorophenyl)cycloheptyl)methyl)-2-methoxybenzamide.

Clause 11. A process for the preparation of a compound of formula (I) as defined in any one of the preceding clauses, the process comprising an amide coupling reaction between the carboxylic acid group of a compound of formula (II) and the amine group of a compound of formula (III):

(II)

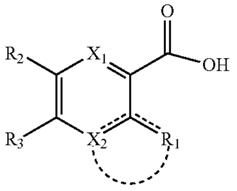

(III)

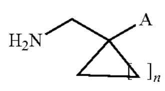

wherein $R_1$ to $R_3$, A, $X_1$, $X_2$ and n are as defined in any of the preceding clauses, in the presence of polar solvent comprising one or more coupling agents.

Clause 12. The process of clause 11, wherein the compound of formula (III) is in molar excess with respect to the compound of formula (II).

Clause 13. The process of any one of the preceding clauses 11-12, wherein the coupling reaction is performed by sequentially adding the compound of formula (II), the compound of formula (III), and the coupling agent(s).

Clause 14. A pharmaceutical composition comprising a therapeutically effective amount of a compound of formula (I) as defined in any one of the preceding clauses 1 to 10, together with one or more pharmaceutically acceptable excipients or carriers.

Clause 15. A compound of formula (I) as defined in any one of the preceding clauses 1 to 9 for use in therapy.

Clause 16. A compound of formula (I) as defined in any one of the preceding clauses 1 to 9, for use in the treatment of an inflammatory condition.

The invention claimed is:

1. A compound of formula (I):

(I)

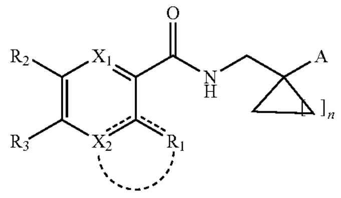

or a pharmaceutically acceptable salt, hydrate, or isomer thereof, wherein:

$R_1$ represents halogen; —$OR_4$; $(C_1$-$C_{10})$alkyl; or $(C_1$-$C_{10})$alkyl substituted with one or more substituents, the same or different, selected from OH, halogen, $(C_1$-$C_6)$alkyl, —O—$(C_1$-$C_6)$alkyl, nitro, cyano, and halogen; or, alternatively, $R_1$ together with $X_2$ forms an aromatic, saturated or partially saturated known ring, the ring having 5 or 6 members selected from the group consisting of: —$C(R_x)_2$—, —$CR_x$—, —N—, —$NR_x$—, S, and O;

- - - represents a single bond or a double bond;

$R_2$ represents —OH; halogen; $(C_1$-$C_{10})$alkyl; $(C_1$-$C_{10})$alkyl substituted with one or more substituents, the same or different, selected from OH, halogen, $(C_1$-$C_6)$alkyl, —O—$(C_1$-$C_6)$alkyl, nitro, cyano, and halogen; —$S(O)_2R_4$; an aromatic known ring system comprising 5 or 6 members selected from —$CR_a$—, and —N—;

$R_3$ represents —$NR_5R_6$, being $R_5$ and $R_6$ the same or different and being selected from —H, $(C_1$-$C_{10})$alkyl, $(C_3$-$C_{10})$cycloalkyl, and an aromatic known ring system comprising 5 or 6 members selected from —$CR_b$—, and —N—; or, alternatively, $R_2$ together with $R_3$ form an aromatic, saturated or partially saturated known ring, the ring having 5 or 6 members selected from —$C(R_y)_2$—, —$CR_y$—, —N—, —$NR_y$, —S—, and —O—;

A is a known ring system having from 1 to 3 rings and comprising from 4 to 14 members, each one of the members being selected from, —$C(R_z)_2$—, —$CR_z$—, —N—, —$NR'_z$—, —S—, —Se—, —$SO_2$, —$SeO_2$, and —O—; the rings being saturated, partially unsaturated, or aromatic; and being fused or isolated; or, alternatively, A represents —$NR_c$-A', wherein $R_c$ represents —H or $(C_1-C_{10})$alkyl, and A' is a known ring system having from 1 to 3 rings and comprising from 4 to 14 members, each one of the members being selected from, —$C(R_z)_2$—, —$CR_z$—, —N—, —$NR_z$—, —S—, —Se—, —$SO_2$, —$SeO_2$, and —O—; the rings being saturated, partially unsaturated, or aromatic; and being fused or isolated;

n represents a enter value comprised from 1 to 7;

$X_1$ and $X_2$ are the same or different and represent C or N atom;

$R_4$ represents —H; $(C_1-C_{10})$ alkyl; or $(C_1-C_{10})$ alkyl substituted with one or more substituents, the same or different, selected from OH, halogen, $(C_1-C_6)$alkyl, —O—$(C_1-C_5)$alkyl, nitro, cyano, and halogen;

the term "$(C_3-C_{10})$cycloalkyl" refers to a saturated carbocyclic ring containing from 3 to 10 carbon atoms;

each one of $R_a$ is independently selected from the group consisting of —H, —OH, halogen, $(C_1-C_6)$alkyl, and $(C_1-C_6)$alkyl substituted with one or more substituents, the same or different, selected from: OH, halogen, $(C_1-C_6)$alkyl, —O—$(C_1-C_6)$alkyl, nitro, cyano, and halogen;

each one of $R_b$ is independently selected from the group consisting of —H, —OH, halogen, $(C_1-C_6)$alkyl, and $(C_1-C_6)$alkyl substituted with one or more substituents, the same or different, selected from: OH, halogen, $(C_1-C_6)$alkyl, —O—$(C_1-C_6)$alkyl, nitro, cyano, and halogen;

$R_t$ represents $(C_1-C_{10})$ alkyl;

each one of the Rx is independently selected from the group consisting of —H, —OH, $(C_1-C_6)$alkyl, $(C_1-C_6)$ haloalkyl, —O—$(C_1-C_6)$alkyl, nitro, —$NR_7$—, —$NR_8R_9$, and halogen;

each one of the Ry is independently selected from the group consisting of —H, —OH, $(C_1-C_6)$alkyl, $(C_1-C_5)$ haloalkyl, —O—$(C_1-C_6)$alkyl, nitro, —$NR_{10}$—, —$NR_{11}R_{12}$, and halogen;

each one of the Rz is independently selected from the group consisting of —H, —OH, $(C_1-C_6)$alkyl, $(C_1-C_6)$ haloalkyl, —O—$(C_1-C_6)$alkyl, —O—$(C_1-C_6)$haloalkyl, nitro, —$NR_{13}$—, —$NR_{12}R_{15}$, and halogen;

$R'_z$ is selected from the group consisting of $(C_1-C_6)$alkyl and $(C_1-C_6)$haloalkyl; and each one of $R_7$ to $R_{15}$ is independently selected from the group consisting of H, $(C_1-C_6)$alkyl, $(C_1-C_6)$haloalkyl, and —O—$(C_1-C_6)$alkyl.

2. The compound of claim 1 which is one of formula (Ia):

(Ia)

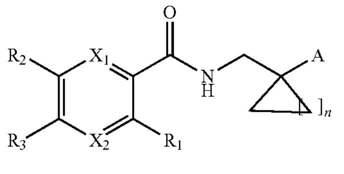

3. The compound of claim 1, wherein $R_1$ is selected from —OH, —O—$(C_1-C_{10})$alkyl, and halogen; or alternatively, $R_1$ together with $X_2$ forms a partially saturated or aromatic known ring having 5 or 6 members, the members being as defined above.

4. The compound of claim 1, wherein $R_2$ represents halogen or —$S(O)_2R_t$.

5. The compound of claim 1, wherein $R_3$ represents —$NR_6R_7$, $R_6$ and $R_7$ being the same, alternatively $R_3$ together with $R_2$ form an aromatic or partially saturated known ring, the ring having 5 or 6 members as defined above.

6. The compound of claim 1, wherein A is selected from:

an aryl ring comprising 5 or 6 members, a saturated ring comprising from 4 to 8 members, and —NH-A', wherein A' is an aryl ring comprising 5 or 6 members.

7. The compound of claim 6, wherein A is selected from:

a known 6-membered aryl wherein one of the members is —N—, and the other members forming the 6-membered ring are —$CR_z$—, each one of the $R_z$ being independently selected from: H, $(C_1-C_6)$haloalkyl, and halogen;

a known 6-membered aryl ring having 6 —$CR_z$— members, each one of the $R_z$ being independently selected from: H, $(C_1-C_6)$haloalkyl, —$NR_7$—, and halogen;

a saturated known 6-membered ring, wherein one or two of the members are selected from —$NR'_z$—, —S—, and —O— and the other members forming part of the ring represent —$C(R_z)_2$—, each one of the $R_z$ being independently selected from: H, $(C_1-C_6)$alkyl, and halogen; and $R'_z$ representing $(C_1-C_6)$alkyl; and —NH-A', wherein A' is a known 6-membered aryl ring having 6 —$CR_z$— members, each one of the $R_z$ being independently selected from: H, $(C_1-C_6)$haloalkyl, halogen and —O—$(C_1-C_6)$haloalkyl.

8. The compound of claim 1, which is selected from the group consisting of:

4-amino-5-chloro-2-methoxy-N-((1-morpholinocycloheptyl)methyl)benzamide;

4-amino-5-(ethylsulfonyl)-2-methoxy-N-((1-morpholinocycloheptyl)methyl)benzamide;

4-amino-5-fluoro-2-methoxy-N-((1-morpholinocycloheptyl)methyl)benzamide;

4-amino-2,5-difluoro-N-((1-morpholinocycloheptyl)methyl)benzamide;

6-amino-5-chloro-2-methoxy-N-((1-morpholinocycloheptyl)methyl)nicotinamide;

6-chloro-N-((1-morpholinocycloheptyl)methyl)imidazo[1,2-a]pyridine-8-carboxamide;

N-((1-morpholinocycloheptyl)methyl)quinoxaline-2-carboxamide;

4-amino-5-chloro-2-hydroxy-N-((1-morpholinocycloheptyl)methyl)benzamide;

4-amino-5-chloro-2-methoxy-N-((1-thiomorpholinocycloheptyl)methyl)benzamide;

4-amino-5-chloro-2-methoxy-N-((1-(4-methylpiperazin-1-yl)cycloheptyl)methyl)benzamide;

4-amino-5-chloro-N-((1-(4-fluoropiperidin-1-yl)cyclohexyl)methyl)-2-methoxybenzamide;

4-amino-5-chloro-N-((1-(4,4-difluoropiperidin-1-yl)cyclohexyl)methyl)-2-methoxybenzamide;

4-amino-5-chloro-N-((1-(4-chlorophenyl)cyclopropyl)methyl)-2-methoxybenzamide;

4-amino-5-chloro-N-((1-(4-chlorophenyl)cyclobutyl)methyl)-2-methoxybenzamide;

4-amino-5-chloro-N-((1-(4-chlorophenyl)cyclopentyl)methyl)-2-methoxybenzamide;

4-amino-5-chloro-N-((1-(4-chlorophenyl)cyclohexyl)methyl)-2-methoxybenzamide;

4-amino-5-chloro-N-((1-(4-chlorophenyl)cycloheptyl)methyl)-2-methoxybenzamide;

4-amino-5-chloro-N-((1-((4-chlorophenyl)amino)cycloheptyl)methyl)-2-methoxybenzamide;
4-amino-5-chloro-N-((1-(3,4-dichlorophenyl)cycloheptyl)methyl)-2-methoxybenzamide;
6-amino-5-chloro-N-((1-(4-chlorophenyl)cycloheptyl) methyl)-2-methoxynicotinamide;
5-amino-6-chloro-N-((1-(4-chlorophenyl)cycloheptyl) methyl)chroman-8-carboxamide;
4-amino-5-chloro-N-((1-(4-fluorophenyl)cycloheptyl) methyl)-2-methoxybenzamide;
4-amino-5-chloro-N-((1-(2-chloro-4-fluorophenyl)cycloheptyl)methyl)-2-methoxybenzamide;
4-amino-5-chloro-2-methoxy-N-((1-(4-(trifluoromethyl) phenyl)cycloheptyl)methyl) benzamide;
4-amino-5-chloro-2-methoxy-N-((1-(5-(trifluoromethyl) pyridin-2-yl)cycloheptyl)methyl) benzamide;
4-amino-5-chloro-2-methoxy-N-((1-(pyridin-3-yl)cycloheptyl)methyl)benzamide;
4-amino-5-chloro-N-((1-((2-chloro-4-fluorophenyl) amino)cycloheptyl)methyl)-2-methoxybenzamide;
4-amino-5-chloro-2-methoxy-N-((1-((3-(trifluoromethoxy)phenyl)amino) cycloheptyl)methyl)benzamide;

and any pharmaceutically acceptable salt, hydrate, and isomer thereof.

9. The compound of formula (I) according to claim 7, which is selected from:

4-amino-5-chloro-2-methoxy-N-((1-thiomorpholinocycloheptyl)methyl)benzamide;
4-amino-5-chloro-N-((1-(4-chlorophenyl)cyclohexyl) methyl)-2-methoxybenzamide;
4-amino-5-chloro-N-((1-(4-chlorophenyl)cycloheptyl) methyl)-2-methoxybenzamide;
4-amino-5-chloro-N-((1-((4-chlorophenyl)amino)cycloheptyl)methyl)-2-methoxybenzamide;
4-amino-5-chloro-N-((1-(3,4-dichlorophenyl)cycloheptyl)methyl)-2-methoxybenzamide;
6-amino-5-chloro-N-((1-(4-chlorophenyl)cycloheptyl) methyl)-2-methoxynicotinamide;
4-amino-5-chloro-N-((1-(4-fluorophenyl)cycloheptyl) methyl)-2-methoxybenzamide;
4-amino-5-chloro-N-((1-(2-chloro-4-fluorophenyl)cycloheptyl)methyl)-2-methoxybenzamide;
4-amino-5-chloro-N-((1-((2-chloro-4-fluorophenyl) amino)cycloheptyl)methyl)-2-methoxybenzamide;
4-amino-5-chloro-2-methoxy-N-((1-((3-(trifluoromethoxy)phenyl)amino) cycloheptyl)methyl)benzamide; and any pharmaceutically acceptable salt, hydrate, and isomer thereof.

10. A pharmaceutical composition comprising a therapeutically effective amount of a compound of formula (I) as defined in claim 1, together with one or more pharmaceutically acceptable excipients or carriers.

11. The compound of claim 1, wherein $R_2$ represents halogen or —$S(O)_2R_t$.

12. The compound of claim 2, wherein A is selected from:

an aryl ring comprising 5 or 6 members, a saturated ring comprising from 4 to 8 members, and —NH-A', wherein A' is an aryl ring comprising 5 or 6 members.

13. The compound of claim 12, wherein A is selected from:

a known 6-membered aryl wherein one of the members is —N—, and the other members forming the 6-membered ring are —$CR_z$—, each one of the $R_z$ being independently selected from: H, $(C_1$-$C_6)$haloalkyl, and halogen;

a known 6-membered aryl ring having 6 —$CR_z$— members, each one of the $R_z$ being independently selected from: H, $(C_1$-$C_6)$haloalkyl, —$NR_7$—, and halogen;

a saturated known 6-membered ring, wherein one or two of the members are selected from —$NR'_z$—, —S—, and —O— and the other members forming part of the ring represent —$C(R_z)_2$—, each one of the $R_z$ being independently selected from: H, $(C_1$-$C_6)$alkyl, and halogen; and $R'_z$ representing $(C_1$-$C_6)$alkyl; and —NH-A', wherein A' is a known 6-membered aryl ring having 6 —$CR_z$— members, each one of the $R_z$ being independently selected from: H, $(C_1$-$C_5)$haloalkyl, halogen and —O—$(C_1$-$C_5)$haloalkyl.

14. A pharmaceutical composition comprising a therapeutically effective amount of a compound of formula (I) as defined in claim 2, together with one or more pharmaceutically acceptable excipients or carriers.

* * * * *